(12) United States Patent  (10) Patent No.: US 8,012,961 B2
Hubschwerlen et al.  (45) Date of Patent: Sep. 6, 2011

(54) TRICYCLIC ANTIBIOTICS

(75) Inventors: Christian Hubschwerlen, Durmenach (FR); Georg Rueedi, Allschwil (CH); John-Philippe Surivet, Kembs (FR); Cornelia Zumbrunn-Acklin, Basel (CH)

(73) Assignee: Actelion Pharmaceutical Ltd., Allschwil (CH)

( * ) Notice: Subject to any disclaimer, the term of this patent is extended or adjusted under 35 U.S.C. 154(b) by 0 days.

(21) Appl. No.: 12/988,205

(22) PCT Filed: Apr. 14, 2009

(86) PCT No.: PCT/IB2009/051541
§ 371 (c)(1),
(2), (4) Date: Oct. 15, 2010

(87) PCT Pub. No.: WO2009/128019
PCT Pub. Date: Oct. 22, 2009

(65) Prior Publication Data
US 2011/0039836 A1  Feb. 17, 2011

(30) Foreign Application Priority Data
Apr. 15, 2008  (WO) .................. PCT/IB2008/051442

(51) Int. Cl.
*C07D 491/048* (2006.01)
*C07D 519/00* (2006.01)
*A61K 31/33* (2006.01)

(52) U.S. Cl. .................... 514/224.2; 514/230.5; 544/48; 544/51; 544/105

(58) Field of Classification Search .................... 544/48, 544/51, 105; 514/224.2, 230.5
See application file for complete search history.

(56) References Cited

FOREIGN PATENT DOCUMENTS

| WO | WO 01/07432 | 2/2001 |
|----|---|---|
| WO | WO 01/07433 | 2/2001 |
| WO | WO 02/08224 | 1/2002 |
| WO | WO 02/56882 | 1/2002 |
| WO | WO 02/24684 | 3/2002 |
| WO | WO 03/064421 | 1/2003 |
| WO | WO 03/087098 | 10/2003 |
| WO | WO 2004/002490 | 1/2004 |
| WO | WO 2004/035569 | 4/2004 |
| WO | WO 2004/058144 | 7/2004 |
| WO | WO 2006/002047 | 1/2006 |
| WO | WO 2006/010040 | 1/2006 |
| WO | WO 2006/010831 | 2/2006 |
| WO | WO 2006/014580 | 2/2006 |
| WO | WO 2006/021448 | 3/2006 |
| WO | WO 2006/032466 | 3/2006 |
| WO | WO 2006/046552 | 5/2006 |
| WO | WO 2006/134378 | 6/2006 |
| WO | WO 2007/042325 | 4/2007 |
| WO | WO 2007/122258 | 4/2007 |
| WO | WO 2007/071936 | 6/2007 |
| WO | WO 2007/081597 | 7/2007 |
| WO | WO 2008/006648 | 1/2008 |

OTHER PUBLICATIONS

Gould, "Salt selection for basic drugs," Int. J. Pharm., 33 (1986), pp. 201-217.

(Continued)

*Primary Examiner* — Kahsay T Habte
(74) *Attorney, Agent, or Firm* — Hunton & Williams LLP

(57) ABSTRACT

The invention relates to antibacterial compounds of formula (I)

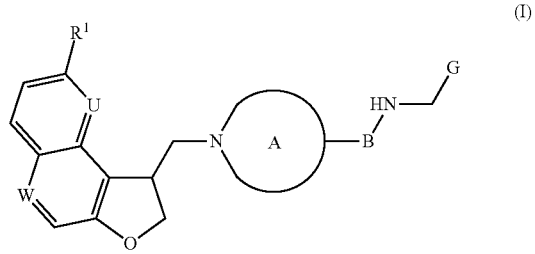

wherein
U represents CH or N; W represents CH or N; $R^1$ represents alkoxy, halogen or CN; ring A represents a pyrrolidin-1,3-diyl-, a piperidin-1,3-diyl or a morpholin-2,4-diyl group and B represents $CH_2$; or ring A is selected from the groups drawn below:

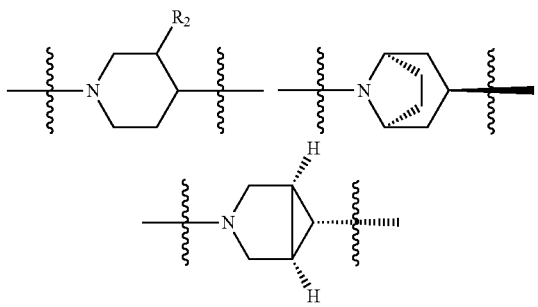

wherein $R^2$ represents H, F or hydroxymethyl, and B is absent;
G represents a group selected from the group consisting of —CH═CH-E,

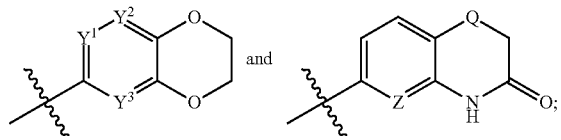

wherein $Y^1, Y^2, Y^3$ and Z independently represent CH or N; Q represents O or S; and E represents phenyl which is mono- or di-substituted wherein the substituents are each independently halogen;
and to pharmaceutically acceptable salts of such compounds.

14 Claims, No Drawings

OTHER PUBLICATIONS

Remington, The Science and Practice of Pharmacy, 21st Edition (2005), Part 5, "Pharmaceutical Manufacturing".

Greene, et al., "Protection for the amino Group Groups in Organic Synthesis", 3rd Ed (1 999), 494-653.

Sato, et al., "One-pot reductive amination of aldehydes and ketones with α-picoline-borane in methanol, in water, and in neat conditions," Tetrahedron (2004), 60,7899-7906.

Larock "Comprehensive Organic Transformations. A guide to Functional Group Preparations," $2^{nd}$ Edition, Wiley-VC; pp. 1075-1111 (1999).

Larock, "Comprehensive Organic Transformations A guide to Functional Group Preparations", $2^{nd}$ Ed., Wiley, pp. 1114-1120 (1999).

Larock, Comprehensive Organic Transformations A guide to Functional Group Preparations:, $2^{nd}$ Ed., Wiley, pp. 1075-1110 (1999).

Mancusco, A., "Oxidation of long-chain and related alcohols to carbonyls by dimethyl sulfoxide "activated" by oxalyl chloride" J. Org. Chem., 1978, 43, (12), pp. 2480-2482.

Dess et al., "Readily accessible 12-1-5 oxidant for the conversion of primary and secondary alcohols to aldehydes and ketones", J. Org. Chem., 1983, 48 (22), pp. 4155-4156.

Kuwabe, et al., "Palladium-Caralyzed Intramolecular C–) Bond Formation," J. Am. Chem. Soc. (2001 ), 123,12202-12206.

TRICYCLIC ANTIBIOTICS

CROSS-REFERENCE TO RELATED APPLICATIONS

This application is the national phase application of PCT/IB2009/051541, filed Apr. 14, 2009, which claims the benefit of PCT/IB2008/051442, filed Apr. 15, 2008, the contents of all of which are hereby incorporated by reference as if fully set forth herein.

FIELD OF THE INVENTION

The present invention concerns novel dihydrofuroquinoline and dihydrofuronaphtyridine antibiotic derivatives, a pharmaceutical antibacterial composition containing them and the use of these compounds in the manufacture of a medicament for the treatment of infections (e.g. bacterial infections). These compounds are useful antimicrobial agents effective against a variety of human and veterinary pathogens including among others Gram positive and Gram negative aerobic and anaerobic bacteria and mycobacteria.

BACKGROUND OF THE INVENTION

The intensive use of antibiotics has exerted a selective evolutionary pressure on micro-organisms to produce genetically based resistance mechanisms. Modern medicine and socio-economic behaviour exacerbates the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumoniae, Enterococcus* spp., and *Pseudomonas aeruginosa*, major sources of infections, are becoming multi-drug resistant and therefore difficult if not impossible to treat:
  *S. aureus* is resistant to β-lactams, quinolones and now even to vancomycin;
  *S. pneumoniae* is becoming resistant to penicillin or quinolone antibiotics and even to new macrolides;
  *Enteroccocci* are quinolone and vancomycin resistant and β-lactam antibiotics are inefficacious against these strains;
  *Enterobacteriacea* are cephalosporin and quinolone resistant;
  *P. aeruginosa* are β-lactam and quinolone resistant.
Further new emerging organisms like *Acinetobacter* spp., *Burkholderia* spp. *Stenotrophomonas maltophilia*, or *Clostridium difficile*, which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

Certain heterocyclic compounds containing a 2-(aminomethyl)-morpholin-4-ylethyl -derived moiety are known as antibacterial agents from WO 2004/035569, WO 2006/014580, WO 2006/021448 and WO 2008/006648.

Certain heterocyclic compounds containing a 3-(aminomethyl)-pyrrolidin-1-ylethyl -derived moiety are known as antibacterial agents from WO 2006/002047 and WO 2008/006648.

Certain heterocyclic compounds containing a 3-(aminomethyl)-piperidin-1-ylethyl -derived moiety are known as antibacterial agents from WO 2004/035569, WO 2006/014580 and WO 2006/021448.

Certain heterocyclic compounds containing a 4-amino-piperidin-1-ylethyl-derived moiety are known as antibacterial agents from WO 01/07432, WO 01/07433, WO 02/08224, WO 02/24684, WO 02/056882, WO 2003/064421, WO 2004/002490, WO 2004/058144, WO 2006/046552, WO 2006/134378, WO 2007/042325 WO 2007/118130 and WO 2008/006648.

Certain heterocyclic compounds containing a 8-ethyl-8-aza-bicyclo[3.2.1]oct-3-ylamino-derived moiety are known as antibacterial agents from WO 2004/035569 and WO 2006/021448.

Moreover, certain heterocyclic compounds containing a 3-ethyl-3-aza-bicyclo[3.1.0]hex-6-ylamino-derived moiety are known as antibacterial agents from WO 2006/010040 and WO 2006/032466.

Various embodiments of the invention are presented hereafter.

DETAILED DESCRIPTION OF PREFERRED EMBODIMENTS

1) A first embodiment of the present invention relates to compounds of formula (I)

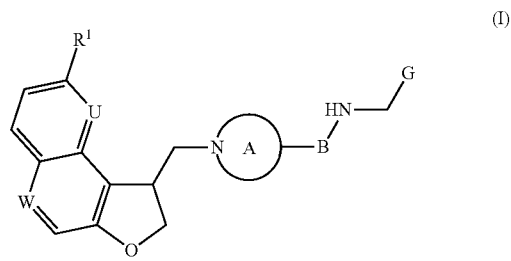

wherein
U represents CH or N;
W represents CH or N;
$R^1$ represents alkoxy, halogen or CN (in particular alkoxy or halogen);
ring A represents a pyrrolidin-1,3-diyl, a piperidin-1,3-diyl or a morpholin-2,4-diyl group and B represents $CH_2$; or ring A is selected from the group consisting of the groups $A^1$, $A^2$ and $A^3$ drawn below:

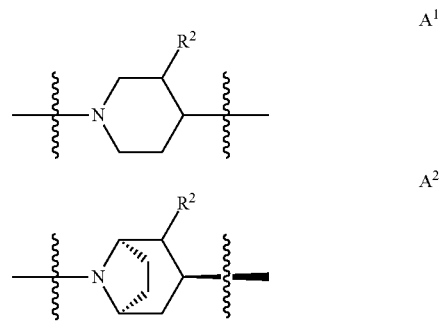

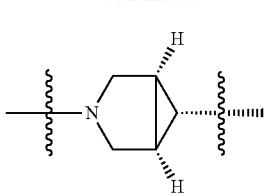

A³ wherein R² represents H, F or hydroxymethyl, and B is absent;

G represents a group selected from the group consisting of

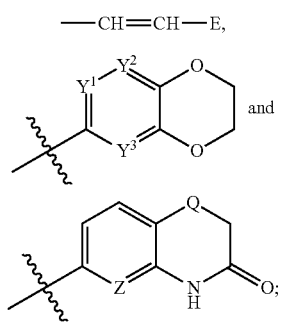

—CH=CH—E, and wherein Y¹, Y², Y³ and Z independently represent CH or N (and notably wherein Z represents CH or N, and Y¹, Y² and Y³ each represent CH, or Y¹ and Y³ each represent CH and Y² represents N, or Y¹ represents N, Y² represents CH or N and Y³ represents CH, or Y¹ and Y² each represent CH and Y³ represents N);

Q represents O or S; and

E represents phenyl which is mono- or di-substituted wherein the substituents are each independently halogen.

The following paragraphs provide definitions of the various chemical moieties for the compounds according to the invention and are intended to apply uniformly throughout the specification and claims, unless an otherwise expressly set out definition provides a broader or narrower definition.

In this patent application, a bond interrupted by a wavy line shows the point of attachment of the radical drawn. For example, the radical drawn below

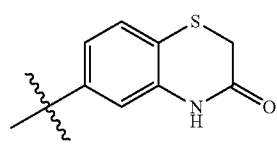

is the 4H-benzo[1,4]thiazin-3-on-6-yl or 3-oxo-3,4-dihydro-2H-benzo[1,4]thiazin-6-yl group.

The term "halogen" refers to fluorine, chlorine, bromine or iodine; especially to fluorine, chlorine or bromine; preferably to fluorine or chlorine, most preferably to fluorine.

The term "alkyl", used alone or in combination, refers to a straight or branched chain alkyl group containing one to four carbon atoms. The term "($C_x$-$C_y$)alkyl" (x and y each being an integer), refers to an alkyl group as defined before containing x to y carbon atoms. For example a ($C_1$-$C_4$)alkyl group contains from one to four carbon atoms. Representative examples of alkyl groups include methyl, ethyl, n-propyl, iso-propyl, n-butyl, iso-butyl, sec-butyl and tert-butyl. Preferred are methyl, ethyl, n-propyl and iso-propyl. Most preferred is methyl.

The term "alkoxy", used alone or in combination, refers to an alkyl-O- group wherein the alkyl group is as defined before. The term "($C_x$-$C_y$)alkoxy" (x and y each being an integer) refers to an alkoxy group as defined before containing x to y carbon atoms. For example a ($C_1$-$C_4$)alkoxy group contains from one to four carbon atoms. Representative examples of alkoxy groups include methoxy, ethoxy, n-propoxy, iso-propoxy, n-butoxy, iso-butoxy, sec-butoxy and tert-butoxy. Preferred are ethoxy and methoxy. Most preferred is methoxy.

In case G represents a group "—CH=CH-E", the double bond of said group may be present in the Z- or E-configuration or in mixtures of E and Z, preferably the double bond is in E-configuration. The group E as used in G representing a group "—CH=CH-E", preferably represents phenyl which is di-substituted wherein the substituents are each independently halogen (especially fluorine). An example of such a group G representing "—CH=CH-E" is 2-(2,5-difluorophenyl)-ethenyl (notably (E)-2-(2,5-difluorophenyl)-ethenyl).

In case G represents a group

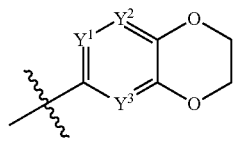

as defined for formula (I) according to embodiment 1), examples of such groups are 2,3-dihydro-benzo[1,4]dioxin-6-yl, 2,3-dihydro-[1,4]dioxino[2,3-b]pyridin-6-yl, 2,3-dihydro-[1,4]dioxino[2,3-c]pyridin-7-yl and 6,7-dihydro-[1,4]dioxino[2,3-c]pyridazin-3-yl.

In case G represents a group

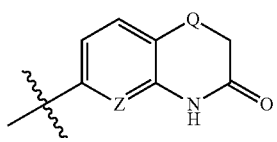

as defined for formula (I) according to embodiment 1), examples of such groups are 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]thiazin-6-yl and 3-oxo-3,4-dihydro-2H-pyrido[3,2-b][1,4]oxazin-6-yl.

In case "ring A represents a pyrrolidin-1,3-diyl, a piperidin-1,3-diyl or a morpholin-2,4-diyl group; and B represents CH₂", such group -A-B— is:

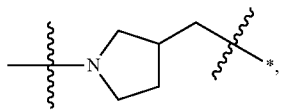

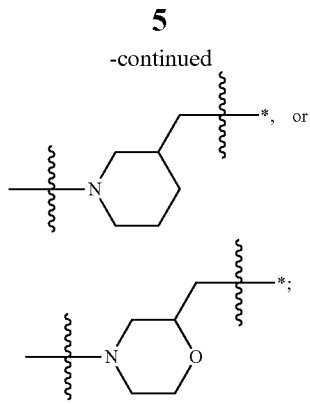, or

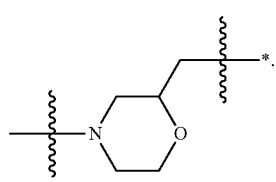;

wherein the asterisks indicate the bond which is linked to the —NH—CH$_2$-G group of the compound of formula (I). Preferably, said group -A-B— is in this case

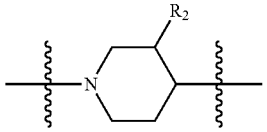.

In a sub-embodiment, the chiral center at the ring A of the above groups is in absolute (R)-configuration. In another sub-embodiment, the chiral center at the ring A of the above groups is in absolute (S)-configuration.

In case "ring A represents the group $A^1$

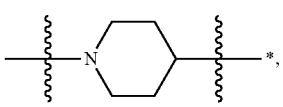

wherein $R^2$ represents H, and B is absent", such group -A-B— is a piperidin-1,4-diyl group:

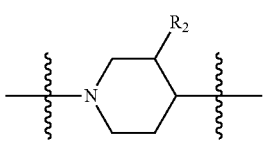, wherein the asterisk indicates the bond which is linked to the —NH—CH$_2$-G group of the compound of formula (I).

In case "ring A represents the group $A^1$

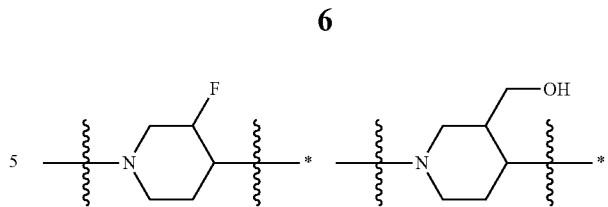

wherein $R^2$ represents F or hydroxymethyl, and B is absent", such group -A-B— is respectively the 3-fluoro-piperidin-1,4-diyl or 3-hydroxymethyl-piperidin-1,4-diyl group represented below:

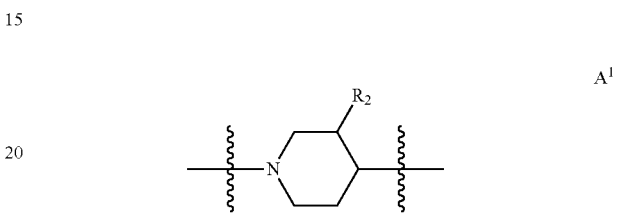

wherein the asterisk indicates the bond which is linked to the —NH—CH$_2$-G group of the compound of formula (I) and the carbon bearing the fluorine or the hydroxymethyl group may be in absolute (S)- or (R)-configuration.

In case "ring A represents the group $A^1$

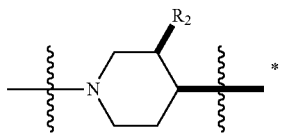

wherein $R^2$ represents F or hydroxymethyl, and B is absent", the group -A-B— will preferably be such that its stereochemistry is as drawn below:

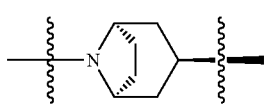

wherein the asterisk indicates the bond which is linked to the —NH—CH$_2$-G group of the compound of formula (I), that is, such that the groups $R^2$ and —NH—CH$_2$-G have the relative cis configuration.

In case "ring A represents the group $A^2$

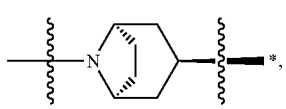

and B is absent", such group -A-B— is a 8-aza-bicyclo[3.2.1]octane-3,8-diyl group:

, wherein the asterisk indicates the bond which is linked to the —NH—CH$_2$-G group of the compound of formula (I).

In case "ring A represents the group $A^3$

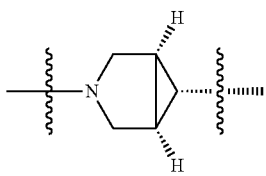

and B is absent", such group -A-B— is a 3-aza-bicyclo[3.1.0]hexane-3,6-diyl group:

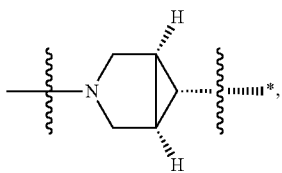

wherein the asterisk indicates the bond which is linked to the —NH—CH$_2$-G group of the compound of formula (I).

Further embodiments of the invention are described hereafter.

2) In particular, the invention relates to compounds of formula (I) as defined in embodiment 1) above that are also compounds of formula (I$_P$)

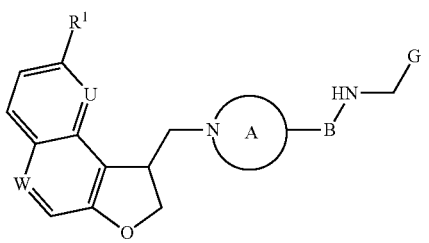

wherein
U represents N;
W represents CH or N;
$R^1$ represents (C$_1$-C$_4$)alkoxy or CN;
ring A represents a pyrrolidin-1,3-diyl, a piperidin-1,3-diyl or a morpholin-2,4-diyl group and B represents CH$_2$; or ring A represents a piperidin-1,4-diyl group and B is absent;
G represents a group selected from the group consisting of —CH═CH-E,

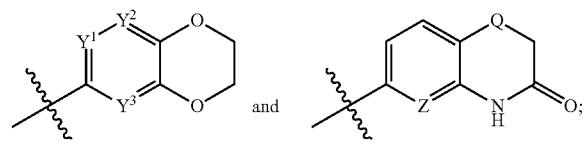

wherein Y$^1$, Y$^2$, Y$^3$ and Z independently represent CH or N;
Q represents O or S; and
E represents phenyl which is mono- or di-substituted wherein the substituents are each independently halogen.

In embodiment 2), in case G represents a group "—CH═CH-E", the double bond of said group may be present in the Z- or E-configuration or in mixtures of E and Z, preferably the double bond is in E-configuration. The group E as used in G representing a group "—CH═CH-E", preferably represents phenyl which is di-substituted wherein the substituents are each independently halogen (especially fluorine). An example of such a group G representing "—CH═CH-E" is 2-(2,5-difluorophenyl)-ethenyl (notably (E)-2-(2,5-difluorophenyl)-ethenyl).

In embodiment 2), in case G represents a group

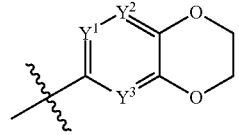

as defined for formula (I) according to embodiment 1), examples of such groups are 2,3-dihydro-benzo[1,4]dioxin-6-yl, 2,3-dihydro-[1,4]dioxino[2,3-b]pyridin-6-yl, 2,3-dihydro-[1,4]dioxino[2,3-c]pyridin-7-yl and 6,7-dihydro-[1,4]dioxino[2,3-c]pyridazin-3-yl.

In embodiment 2), in case G represents a group

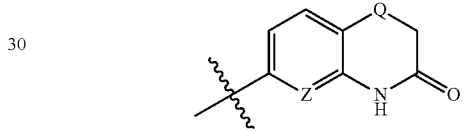

as defined for formula (I) according to embodiment 1), examples of such groups are 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]thiazin-6-yl and 3-oxo-3,4-dihydro-2H-pyrido[3,2-b][1,4]oxazin-6-yl.

In embodiment 2), in case "ring A represents a pyrrolidin-1,3-diyl, a piperidin-1,3-diyl or a morpholin-2,4-diyl group; and B represents CH$_2$", such group -A-B— is:

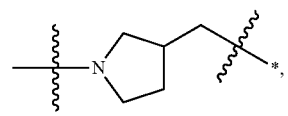

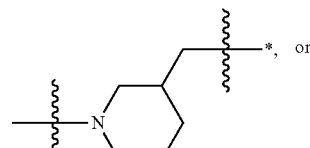

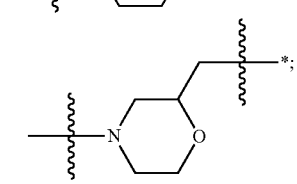

wherein the asterisks indicate the bond which is linked to the —NH—CH$_2$-G group of the compound of formula (I). In this case, said group -A-B— will notably be

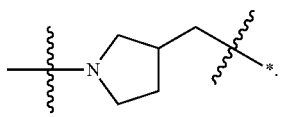

In a sub-embodiment of embodiment 2), the chiral center at the ring A of the above groups is in absolute (R)-configuration. In another sub-embodiment of embodiment 2), the chiral center at the ring A of the above groups is in absolute (S)-configuration.

In embodiment 2), in case "ring A represents a piperidin-1,4-diyl group, and B is absent", such group -A-B— is a piperidin-1,4-diyl group:

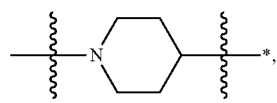

wherein the asterisk indicates the bond which is linked to the —NH—CH$_2$-G group of the compound of formula (I).

3) A further embodiment of the invention relates to compounds according to embodiment 1) or 2), wherein the stereocenter at position 9 of the 8,9-dihydro-furo[2,3-h]quinolin-9-ylmethyl group or the stereocenter at position 1 of the 1,2-dihydro-3-oxa-5,9-diaza-cyclopenta[a]naphthalen-1-yl-methyl group is in (R)-configuration:

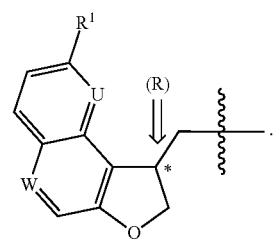

4) A further embodiment of the invention relates to compounds according to embodiment 1) or 2), wherein the stereocenter at position 9 of the 8,9-dihydro-furo[2,3-h]quinolin-9-ylmethyl group or the stereocenter at position 1 of the 1,2-dihydro-3-oxa-5,9-diaza-cyclopenta[a]naphthalen-1-yl-methyl group is in (S)-configuration:

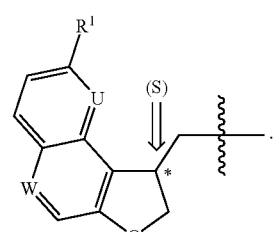

5) A further embodiment of the invention relates to compounds according to any one of embodiments 1) to 4), wherein W represents N.

6) A further embodiment of the invention relates to compounds according to any one of embodiments 1) to 4), wherein W represents CH.

7) A further embodiment of the invention relates to compounds according to embodiment 1), or to embodiment 1) taken together with any of embodiments 3) to 6), wherein R$^1$ represents alkoxy or halogen (especially methoxy or fluorine).

8) A further embodiment of the invention relates to compounds according to any one of embodiments 1) to 7), wherein R$^1$ represents alkoxy (especially methoxy).

9) A further embodiment of the invention relates to compounds according to one of embodiments 1) to 8), wherein ring A represents a pyrrolidin-1,3-diyl, a piperidin-1,3-diyl or a morpholin-2,4-diyl group and B represents CH$_2$.

10) A further embodiment of the invention relates to compounds according to embodiment 1), or to embodiment 1) taken together with any of embodiments 3) to 8), wherein ring A is selected from the group consisting of the groans A$^1$, A$^2$ and A$^3$ drawn below:

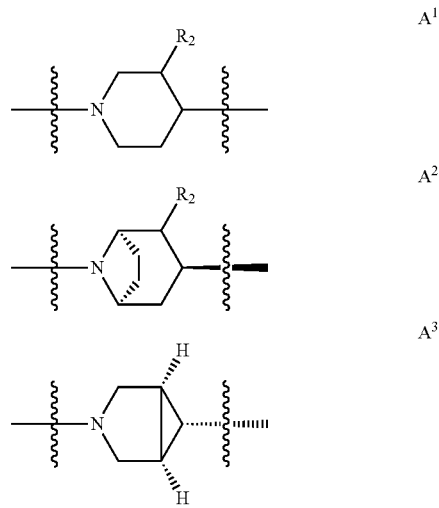

wherein R$^2$ represents H, F or hydroxymethyl (and notably H), and B is absent.

11) According to a variant of embodiment 10), the compounds according to embodiment 10) will be such that ring A is the group A$^1$ wherein R$^2$ represents H, F or hydroxymethyl (and notably H), and B is absent, it being understood that when R$^2$ represents F or hydroxymethyl, the group A$^1$ will preferably be such that its stereochemistry is as drawn below:

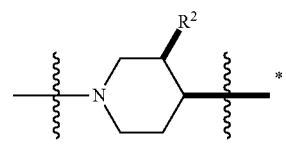

wherein the asterisk indicates the bond which is linked to the —NH—CH$_2$-G group of the compound of formula (I), that is, such that the groups R$^2$ and —NH—CH$_2$-G have the relative cis configuration.

12) According to another variant of embodiment 10), the compounds according to embodiment 10) will be such that ring A is the group A$^2$ and B is absent.

13) According to yet another variant of embodiment 10), the compounds according to embodiment 10) will be such that ring A is the group A$^3$ and B is absent.

14) A further embodiment of the invention relates to compounds according to any one of embodiments 1) to 8), wherein:

ring A represents a pyrrolidin-1,3-diyl group and B represents $CH_2$; or ring A represents a piperidin-1,4-diyl group and B is absent.

15) A further embodiment of the invention relates to compounds according to any one of embodiments 1) to 8), wherein ring A represents a pyrrolidin-1,3-diyl group and B represents $CH_2$.

16) A further embodiment of the invention relates to compounds according to any one of embodiments 1) to 8), 10) and 11) wherein ring A represents a piperidin-1,4-diyl group and B is absent.

17) A further embodiment of the invention relates to compounds according to any one of embodiments 1) to 16), wherein G represents a group selected from the group consisting of

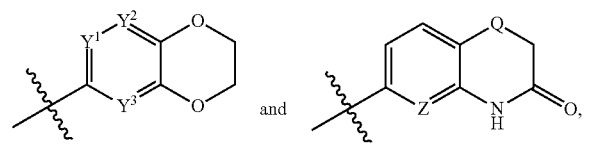

wherein $Y^1, Y^2, Y^3$ and Z independently represent CH or N (and notably wherein Z represents CH or N, and $Y^1, Y^2$ and $Y^3$ each represent CH, or $Y^1$ and $Y^3$ each represent CH and $Y^2$ represents N, or $Y^1$ represents N, $Y^2$ represents CH or N and $Y^3$ represents CH, or $Y^1$ and $Y^2$ each represent CH and $Y^3$ represents N); and Q represents O or S.

18) A further embodiment of the invention relates to compounds according to any one of embodiments 1) to 17), wherein G represents a group selected from the group consisting of 2,3-dihydro-benzo[1,4]dioxin-6-yl, 2,3-dihydro-[1,4]dioxino[2,3-b]pyridin-6-yl, 2,3-dihydro-[1,4]dioxino[2,3-c]pyridin-7-yl, 6,7-dihydro-[1,4]dioxino[2,3-c]pyridazin-3-yl, 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]thiazin-6-yl and 3-oxo-3,4-dihydro-2H-pyrido[3,2-b][1,4]oxazin-6-yl.

19) A further embodiment of the invention relates to compounds according to any one of embodiments 1) to 17), wherein G represents

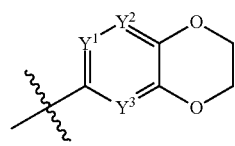

wherein $Y^1, Y^2,$ and $Y^3$ independently represent CH or N (and notably wherein $Y^1, Y^2$ and $Y^3$ each represent CH, or $Y^1$ and $Y^3$ each represent CH and $Y^2$ represents N, or $Y^1$ represents N, $Y^2$ represents CH or N and $Y^3$ represents CH, or $Y^1$ and $Y^2$ each represent CH and $Y^3$ represents N).

20) A further embodiment of the invention relates to compounds according to any one of embodiments 1) to 19), wherein G represents a group selected from the group consisting of 2,3-dihydro-benzo[1,4]dioxin-6-yl, 2,3-dihydro-[1,4]dioxino[2,3-b]pyridin-6-yl, 2,3-dihydro-[1,4]dioxino[2,3-c]pyridin-7-yl and 6,7-dihydro-[1,4]dioxino[2,3-c]pyridazin-3-yl.

21) A further embodiment of the invention relates to compounds according to any one of embodiments 1) to 17), wherein G represents

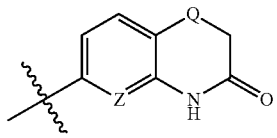

wherein Z represents CH or N; and Q represents O or S.

22) A further embodiment of the invention relates to compounds according to any one of embodiments 1) to 17), wherein G represents

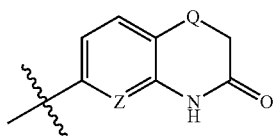

wherein Z represents CH.

23) A further embodiment of the invention relates to compounds according to any one of embodiments 1) to 17), wherein G represents

wherein Z represents N.

24) A further embodiment of the invention relates to compounds according to any one of embodiments 1) to 17), 22) and 23), wherein G represents

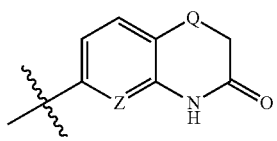

wherein Q represents S.

25) A further embodiment of the invention relates to compounds according to any one of embodiments 1) to 14), 22) and 23), wherein G represents

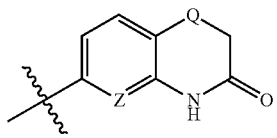

wherein Q represents O.

26) A further embodiment of the invention relates to compounds according to any one of embodiments 1) to 18) and 21), wherein G represents a group selected from the group consisting of 3-oxo-3,4-dihydro-2H-benzo[1,4]oxazin-6-yl, 3-oxo-3,4-dihydro-2H-benzo[1,4]thiazin-6-yl, 3-oxo-3,4-dihydro-2H-pyrido[3,2-b][1,4]thiazin-6-yl and 3-oxo-3,4-dihydro-2H-pyrido[3,2-b][1,4]oxazin-6-yl.

27) A further embodiment of the invention relates to compounds according to any one of embodiments 1) to 16), wherein G represents —CH═CH-E, and E represents phenyl which is mono- or di-substituted wherein the substituents are each independently halogen.

28) A further embodiment of the invention relates to compounds according to any one of embodiments 1) to 16) or 27), wherein E represents phenyl which di-substituted wherein the substituents are each independently halogen (notably fluorine), and in particular wherein E represents 2,5-difluoro-phenyl.

29) A further embodiment of the invention relates to compounds according to embodiment 1), or to embodiment 1) taken together with any of embodiments 3) to 28), wherein U represents CH.

30) A further embodiment of the invention relates to compounds according to embodiment 1), or to embodiment 1) taken together with any of embodiments 3) to 28), wherein U represents N.

31) Yet a further embodiment of the invention relates to compounds according to embodiment 1), or to embodiment 1) taken together with any of embodiments 3) to 28), wherein one of U and W represents CH or N and the other represents N (that is, wherein U represents CH and W represents N, U represents N and W represents CH or each of U and W represents N).

32) Yet a further embodiment of the invention relates to compounds according to embodiment 31), wherein U represents CH and W represents N.

33) Yet a further embodiment of the invention relates to compounds according to embodiment 31), wherein U represents N and W represents CH.

34) Yet a further embodiment of the invention relates to compounds according to embodiment 31), wherein each of U and W represents N.

35) Preferred compounds of formula (I) according to embodiment 1) or 2) are selected from the group consisting of:

[(E)-3-(2,5-difluoro-phenyl)-allyl]-[1-(2-methoxy-8,9-dihydro-furo[2,3-h]quinolin-9-ylmethyl)-piperidin-4-yl]-amine;

(2,3-dihydro-[1,4]dioxino[2,3-c]pyridin-7-ylmethyl)-[1-(2-methoxy-8,9-dihydro-furo[2,3-h]quinolin-9-ylmethyl)-piperidin-4-yl]-amine;

(6,7-dihydro-[1,4]dioxino[2,3-c]pyridazin-3-ylmethyl)-[1-(2-methoxy-8,9-dihydro-furo[2,3-h]quinolin-9-ylmethyl)-piperidin-4-yl]-amine;

6-{[1-(2-methoxy-8,9-dihydro-furo[2,3-h]quinolin-9-ylmethyl)-piperidin-4-ylamino]-methyl}-4H-pyrido[3,2-b][1,4]thiazin-3-one;

-6-{[1-(2-methoxy-8,9-dihydro-furo[2,3-h]quinolin-9-ylmethyl)-piperidin-4-ylamino]-methyl}-4H-pyrido[3,2-b][1,4]oxazin-3-one;

6-{[1-(8-methoxy-1,2-dihydro-3-oxa-5,9-diaza-cyclopenta[a]naphthalen-1-ylmethyl) -piperidin-4-ylamino]-methyl}-4H-pyrido[3,2-b][1,4]oxazin-3-one;

6-{[1-(8-methoxy-1,2-dihydro-3-oxa-5,9-diaza-cyclopenta[a]naphthalen-1-ylmethyl) -piperidin-4-ylamino]-methyl}-4H-pyrido[3,2-b][1,4]thiazin-3-one;

(6,7-dihydro-[1,4]dioxino[2,3-c]pyridazin-3-ylmethyl)-[1-(8-methoxy-1,2-dihydro-3-oxa-5,9-diaza-cyclopenta[a]naphthalen-1-ylmethyl)-piperidin-4-yl]-amine;

(2,3-dihydro-[1,4]dioxino[2,3-c]pyridin-7-ylmethyl)-[1-(8-methoxy-1,2-dihydro-3-oxa-5,9-diaza-cyclopenta[a]naphthalen-1-ylmethyl)-piperidin-4-yl]-amine;

(2,3-dihydro-benzo[1,4]dioxin-6-ylmethyl)-[1-(8-methoxy-1,2-dihydro-3-oxa-5,9-diaza -cyclopenta[a]naphthalen-1-ylmethyl)-piperidin-4-yl]-amine;

(2,3-dihydro-[1,4]dioxino[2,3-b]pyridin-6-ylmethyl)-[1-(2-methoxy-8,9-dihydro-furo[2,3-h]quinolin-9-ylmethyl)-piperidin-4-yl]-amine;

(2,3-dihydro-[1,4]dioxino[2,3-c]pyridin-7-ylmethyl)-[(3S)-1-(8-methoxy-1,2-dihydro-3-oxa-5,9-diaza-cyclopenta[a]naphthalen-1-ylmethyl)-pyrrolidin-3-ylmethyl]-amine (and notably (2,3-dihydro-[1,4]dioxino[2,3-c]pyridin-7-ylmethyl)-[(3S)-1-((1RS)-8-methoxy-1,2-dihydro-3-oxo-5,9-diaza-cyclopenta[a]naphthalen-1-ylmethyl)-pyrrolidin-3-ylmethyl]-amine);

[(E)-3-(2,5-difluoro-phenyl)-allyl]-[(3S)-1-(8-methoxy-1,2-dihydro-3-oxa-5,9-diaza -cyclopenta[a]naphthalen-1-ylmethyl)-pyrrolidin-3-ylmethyl]-amine;

6-({[(3S)-1-(8-methoxy-1,2-dihydro-3-oxa-5,9-diaza-cyclopenta[a]naphthalen-1-ylmethyl) -pyrrolidin-3-ylmethyl]-amino}-methyl)-4H-pyrido[3,2-b][1,4]thiazin-3-one; and 6-{[1-(2-methoxy-8,9-dihydro-furo[2,3-h]quinolin-9-ylmethyl)-piperidin-4-ylamino]-methyl}-4H-benzo[1,4]oxazin-3-one;

wherein it is well understood that the 8,9-dihydro-furo[2,3-h]quinolin-9-ylmethyl or 1,2-dihydro-3-oxa-5,9-diaza-cyclopenta[a]naphthalen-1-ylmethyl moiety of the above-listed compounds may be in absolute (R)- or (S)-configuration.

36) Moreover, preferred compounds of formula (I) according to embodiment 1) are selected from the group consisting of:

6-{[1-((1R)-8-methoxy-1,2-dihydro-3-oxa-5,9-diaza-cyclopenta [a]naphthalen-1-ylmethyl) -piperidin-4-ylamino]-methyl}-4H-pyrido[3,2-b][1,4]thiazin-3-one;

6-{[1-((1S)-8-methoxy-1,2-dihydro-3-oxa-5,9-diaza-cyclopenta[a]naphthalen-1-ylmethyl) -piperidin-4-ylamino]-methyl}-4H-pyrido[3,2-b][1,4]thiazin-3-one;

6-{[(3S*,4R*)-3-fluoro-1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one;

6-{[(3S*,4R*)-3-fluoro-1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one;

(2,3-dihydro-[1,4]dioxino [2,3-c]pyridin-7-ylmethyl)-[(3S*,4R*)-3-fluoro-1-(8-methoxy-1,2-dihydro-3-oxa-5,9-diaza-cyclopenta[a]naphthalen-1-ylmethyl)-piperidin-4-yl]-amine;

(2,3-dihydro-[1,4]dioxino[2,3-c]pyridin-7-ylmethyl)-[(3-exo)-8-((8-methoxy-1,2-dihydro-3-oxo-5,9-diaza-cyclopenta[a]naphthalen-1-ylmethyl)-8-aza-bicyclo[3.2.1]oct-3-yl]amine;

[(E)-3-(2,5-difluoro-phenyl)-allyl]-[(3-exo)-8-(8-methoxy-1,2-dihydro-3-oxa-5,9-diaza -cyclopenta[a]naphthalen-1-ylmethyl)-8-aza-bicyclo[3.2.1]oct-3-yl]-amine;

6-{[(3-exo)-8-(8-methoxy-1,2-dihydro-3-oxa-5,9-diaza-cyclopenta[a]naphthalen-1-ylmethyl)-8-aza-bicyclo[3.2.1]oct-3-ylamino]-methyl}-4H-pyrido[3,2-b][1,4]oxazin-3-one;

6-{[(3-exo)-8-(8-methoxy-1,2-dihydro-3-oxa-5,9-diaza-cyclopenta[a]naphthalen-1-ylmethyl)-8-aza-bicyclo[3.2.1]oct-3-ylamino]-methyl}-4H-pyrido[3,2-b][1,4]thiazin-3-one;

6-({[(2S)-4-(8-methoxy-1,2-dihydro-3-oxa-5,9-diaza-cyclopenta[a]naphthalen-1-ylmethyl)-morpholin-2-ylmethyl]-amino}-methyl)-4H-pyrido[3,2-b][1,4]oxazin-3-one;

6-({[(2S)-4-(8-methoxy-1,2-dihydro-3-oxa-5,9-diaza-cyclopenta[a]naphthalen-1-ylmethyl)-morpholin-2-ylmethyl]-amino}-methyl)-4H-pyrido[3,2-b][1,4]thiazin-3-one;

(2,3-dihydro-[1,4]dioxin[2,3-c]pyridin-7-ylmethyl)-[(2S)-4-((8-methoxy-1,2-dihydro-3-oxa-5,9-diaza-cyclopenta[a]naphthalen-1-ylmethyl)-morpholin-2-ylmethyl]amine;

6-({[(3S)-1-(8-methoxy-1,2-dihydro-3-oxa-5,9-diaza-cyclopenta[a]naphthalen-1-ylmethyl)-piperidin-3-ylmethyl]amino}-methyl)-4H-pyrido[3,2-b][1,4]oxazin-3-one;

6-({[(3S)-1-(8-methoxy-1,2-dihydro-3-oxa-5,9-diaza-cyclopenta[a]naphthalen-1-ylmethyl)-piperidin-3-ylmethyl]amino}-methyl)-4H-pyrido[3,2-b][1,4]thiazin-3-one;

(2,3-dihydro-[1,4]dioxino[2,3-c]pyridin-7-ylmethyl)-[(3S)-1-(8-methoxy-1,2-dihydro-3-oxa-5,9-diaza-cyclopenta[a]naphthalen-1-ylmethyl)-piperidin-3-ylmethyl]-amine;

[(E)-3-(2,5-difluoro-phenyl)-allyl]-[(3S)-1-(8-methoxy-1,2-dihydro-3-oxa-5,9-diaza-cyclopenta[a]naphthalen-1-ylmethyl)-piperidin-3-ylmethyl]-amine;

6-({[(3S)-1-(8-methoxy-1,2-dihydro-3-oxa-5,9-diaza-cyclopenta[a]naphthalen-1-ylmethyl)-piperidin-3-ylmethyl]amino}-methyl)-4H-benzo[1,4]oxazin-3-one;

6-{[(1α,5α,6α)-3-(8-methoxy-1,2-dihydro-3-oxa-5,9-diaza-cyclopenta[a]naphthalen-1-ylmethyl)-3-aza-bicyclo[3.1.0]hex-6-ylamino]-methyl}-4H-pyrido[3,2-b][1,4]oxazin-3-one;

(2,3-dihydro-[1,4]dioxino[2,3-c]pyridin-7-ylmethyl)-[(1α,5α,6α)-3-(8-methoxy-1,2-dihydro-3-oxa-5,9-diaza-cyclopenta[a]naphthalen-1-ylmethyl)-3-aza-bicyclo[3.1.0]hex-6-yl]amine;

6-{[(1α,5 α,6 α)-3-(8-methoxy-1,2-dihydro-3-oxa-5,9-diaza-cyclopenta[a]naphthalen-1-ylmethyl)-3-aza-bicyclo[3.1.0]hex-6-ylamino]-methyl}-4H-pyrido[3,2-b][1,4]thiazin-3-one;

6-{[1-(8-fluoro-1,2-dihydro-furo[2,3-c]quinolin-1-ylmethyl)-piperidin-4-ylamino]-methyl}-4H-pyrido[3,2-b][1,4]oxazin-3-one;

6-{(3R*,4S*)-[3-hydroxymethyl-1-(8-methoxy-1,2-dihydro-3-oxa-5,9-diaza-cyclopenta [a]naphthalen-1-ylmethyl)-piperidin-4-ylamino]-methyl}-4H-pyrido[3,2-b][1,4]thiazin-3-one;

6-{(3R*,4S*)-[3-hydroxymethyl-1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one;

(3R*,4S*)-[4-[(6,7-dihydro-[1,4]dioxino[2,3-c]pyridazin-3-ylmethyl)-amino]-1-(8-methoxy -1,2-dihydro-3-oxa-5,9-diaza-cyclopenta[a]naphthalen-1-ylmethyl) -piperidin-3-yl]-methanol;

(6,7-dihydro-[1,4]dioxino[2,3-c]pyridazin-3-ylmethyl)-[(3S)-1-(8-methoxy-1,2-dihydro-3-oxa-5,9-diaza-cyclopenta[a]naphthalen-1-ylmethyl)-piperidin-3-ylmethyl]-amine; and

[4-[(2,3-dihydro-[1,4]dioxino[2,3-c]pyridin-7-ylmethyl)-amino]-1-((S)-8-methoxy-1,2-dihydro-3-oxa-5,9-diaza-cyclopenta[a]naphthalen-1-ylmethyl) -piperidin-3-yl]-methanol;

wherein it is well understood that, unless specified otherwise, the 8,9-dihydro -furo[2,3-h]quinolin-9-ylmethyl, 1,2-dihydro-3-oxa-5,9-diaza -cyclopenta[a]naphthalen-1-ylmethyl or 1,2-dihydro-furo[2,3-c]quinolin-1-ylmethyl moiety of the above-listed compounds may be in absolute (R)- or (S)-configuration.

37) The invention further relates to the compounds of formula (I) as defined in embodiment 1) which are selected from the group consisting of the compounds listed in embodiment 35) and the compounds listed in embodiment 36).

The compounds of formula (I) according to embodiment 1) may contain one or more stereogenic or asymmetric centers, such as one or more asymmetric carbon atoms. The compounds of formula (I) may thus be present as mixtures of stereoisomers or preferably as pure stereoisomers. Mixtures of stereoisomers may be separated in a manner known to a person skilled in the art.

The present invention also relates to pharmacologically acceptable salts and to compositions and formulations of compounds of formula (I) according to embodiment 1).

Any reference to a compound of formula (I) according to any one of embodiments 1) to 37) is to be understood as referring also to the salts (and especially the pharmaceutically acceptable salts) of such compounds, as appropriate and expedient.

The term "pharmaceutically acceptable salts" refers to non-toxic, inorganic or organic acid and/or base addition salts. Reference can be made to "Salt selection for basic drugs", *Int. J. Pharm.* (1986), 33, 201-217.

A pharmaceutical composition according to the present invention contains at least one compound of formula (I) according to one of embodiments 1) to 37) (or a pharmaceutically acceptable salt thereof) as the active agent and optionally carriers and/or diluents and/or adjuvants, and may also contain additional known antibiotics.

As mentioned above, therapeutically useful agents that contain compounds of formula (I) according to one of embodiments 1) to 37), their salts and formulations thereof are also comprised in the scope of the present invention.

The compounds of formula (I) according to any of embodiments 1) to 37) and their pharmaceutically acceptable salts can be used as medicaments, e.g. in the form of pharmaceutical compositions for enteral or parenteral administration.

The production of the pharmaceutical compositions can be effected in a manner which will be familiar to any person skilled in the art (see for example Remington, *The Science and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The compounds of formula (I) according to one of embodiments 1) to 37) are suitable for the use as chemotherapeutic active compounds in human and veterinary medicine and as substances for preserving inorganic and organic materials in particular all types of organic materials for example polymers, lubricants, paints, fibres, leather, paper and wood.

These compounds according to the invention are particularly active against bacteria and bacteria-like organisms.

They are therefore particularly suitable in human and veterinary medicine for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casseliflavus, S. epidermidis, S. haemolyticus,* or *Peptostreptococcus* spp.; pharyngitis, rheumatic fever, and glomerulonephritis related to infection by *Streptococcus pyogenes,* Groups C and G streptococci, *Corynebacterium diphtheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans,* including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus,* coagulase-negative staphylococci (i.e., *S. epidermidis, S. haemolyticus,* etc.), *Streptococcus pyogenes, Streptococcus agalactiae,* Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus,* coagulase-negative staphylococcal species, or *Enterococcus* spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; infections caused by *Mycobacterium tuberculosis, M. leprae, M. paratuberculosis, M. kansasii,* or *M. chelonei*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter pylori* or *Chlamydia pneumoniae.*

The compounds of formula (I) according to one of embodiments 1) to 37) are further useful for the preparation of a medicament for the treatment of infections that are mediated by bacteria such as *E. coli, Klebsiella pneumoniae* and other Enterobacteriaceae, *Acinetobacter* spp., *Stenothrophomonas maltophilia, Neisseria meningitidis, Bacillus cereus, Bacillus anthracis, Clostridium difficile, Corynebacterium* spp., *Propionibacterium acnes* and bacteroide spp.

The compounds of formula (I) according to one of embodiments 1) to 37) are further useful to treat protozoal infections caused by *Plasmodium malaria, Plasmodium falciparum, Toxoplasma gondii, Pneumocystis carinii, Trypanosoma brucei* and *Leishmania* spp.

The present list of pathogens is to be interpreted merely as examples and in no way as limiting.

One aspect of this invention therefore relates to the use of a compound of formula (I) according to one of embodiments 1) to 37), or of a pharmaceutically acceptable salt thereof, for the manufacture of a medicament for the prevention or treatment of a bacterial infection. Another aspect of this invention relates to a compound of formula (I) according to one of embodiments 1) to 37), or of a pharmaceutically acceptable salt thereof, for the prevention or treatment of a bacterial infection.

Accordingly, the compounds of formula (I) according to one of embodiments 1) to 37), or the pharmaceutically acceptable salts thereof, may be used for the preparation of a medicament, and are suitable, for the prevention or treatment of a bacterial infection selected from the group consisting of respiratory tract infections, otitis media, meningitis, skin and soft tissue infections (whether complicated or uncomplicated), pneumonia (including hospital acquired pneumonia), bacteremia, endocarditis, intraabdominal infections, gastrointestinal infections, *Clostridium difficile* infections, urinary tract infections, sexually transmitted infections, foreign body infections, osteomyelitis, lyme disease, topical infections, opthalmological infections, tuberculosis and tropical diseases (e.g. malaria), and notably for the prevention or treatment of a bacterial infection selected from the group consisting of respiratory tract infections, otitis media, meningitis, skin and soft tissue infections (whether complicated or uncomplicated), pneumonia (including hospital acquired pneumonia) and bacteremia.

As well as in humans, bacterial infections can also be treated using compounds of formula (I) according to one of embodiments 1) to 37) (or pharmaceutically acceptable salts thereof) in other species like pigs, ruminants, horses, dogs, cats and poultry.

Another aspect of the invention concerns a method for the prevention or the treatment of a bacterial infection in a patient comprising the administration to said patient of a pharmaceutically active amount of a compound of formula (I) according to one of embodiments 1) to 37), or a pharmaceutically acceptable salt thereof.

Moreover, the compounds of formula (I) according to one of embodiments 1) to 37) may also be used for cleaning purposes, e.g. to remove pathogenic microbes and bacteria from surgical instruments, catheters and artificial implants or to make a room or an area aseptic. For such purposes, the compounds of formula (I) could be contained in a solution or in a spray formulation.

Where the plural form is used for compounds, salts, pharmaceutical compositions, diseases and the like, this is intended to mean also a single compound, salt, or the like.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" (rt) as used herein refers to a temperature of about 25° C.

The compounds of formula (I) can be manufactured in accordance with the present invention using the procedures described hereafter.

Preparation of the Compounds of Formula (I)

Abbreviations:

The following abbreviations are used throughout the specification and the examples:

| | |
|---|---|
| Ac | acetyl (such as in OAc = acetoxy) |
| AcOH | acetic acid |
| Alloc | allyloxycarbonyl |
| aq. | aqueous |
| Boc | tert-butoxycarbonyl |
| t-Bu | tert-butyl |
| Cbz | benzyloxycarbonyl |
| CC | flash column chromatography on silica gel |
| DCE | 1,2-dichloroethane |
| DCM | dichloromethane |
| DIBAH | diisobutylaluminium hydride |
| DMAP | 4-dimethylaminopyridine |
| DMF | N,N-dimethylformamide |
| DMSO | dimethylsulfoxide |
| EA | ethyl acetate |
| ESI | Electron Spray Ionisation |
| eq. | equivalent |
| ether | diethyl ether |
| Et | ethyl |
| EtOH | ethanol |
| Fmoc | 9-fluorenylmethoxycarbonyl |
| Hept | heptane |
| Hex | hexane |
| Me | methyl |
| MeCN | acetonitrile |
| MeOH | methanol |
| m.p. | melting point |
| MS | Mass Spectroscopy |
| Ms | methanesulfonyl, mesyl |
| org. | organic |
| Pd/C | palladium on carbon |
| Ph | phenyl |
| rac | racemic |
| rt | room temperature |
| sat. | saturated |
| t-BuOK | potassium tert-butoxide |
| TEA | triethylamine |
| Tf | trifluoromethanesulfonyl, triflyl |
| TFA | trifluoroacetic acid |
| THF | tetrahydrofuran |
| TMG | 1,1,3,3-tetramethylguanidine |
| Ts | para-toluenesulfonyl, tosyl |
| p-TsCl | para-toluenesulfonyl chloride |

General Reaction Techniques:

General Reaction Technique 1: Amine Protection:

Amines are usually protected as carbamates such as Alloc, Cbz, Boc or Fmoc. They are obtained by reacting the amine with allyl or benzyl chloroformate, di-tert-butyl dicarbonate or Fmoc-Cl in presence of a base such as NaOH, TEA, DMAP or imidazole. They can also be protected as N-benzyl derivatives by reaction with benzyl bromide or chloride in presence of a base such as $Na_2CO_3$ or TEA. Alternatively, N-benzyl derivatives can be obtained through reductive amination in presence of benzaldehyde and a borohydride reagent such as $NaBH_4$, $NaBH_3CN$ or $NaBH(OAc)_3$ in a solvent such as EtOH. Further strategies to introduce other amine protecting groups have been described in *Protecting Groups in Organic Synthesis*, 3rd Ed (1999), 494-653; T. W. Greene, P. G. M. Wuts (Publisher: John Wiley and Sons, Inc., New York, N.Y.).

General Reaction Technique 2: Reductive Amination

The reaction between the amine and the aldehyde or ketone is performed in a solvent system allowing the removal of the formed water through physical or chemical means (e.g. distillation of the solvent-water azeotrope or presence of drying agents such as molecular sieves, $MgSO_4$ or $Na_2SO_4$). Such solvent is typically toluene, Hex, THF, DCM or DCE or mixture of solvents such as MeOH-DCE. The reaction can be catalyzed by traces of acid (usually AcOH). The intermediate imine is reduced with a suitable reducing agent (e.g. $NaBH_4$, $NaBH_3CN$, or $NaBH(OAc)_3$ or through hydrogenation over a noble catalyst such as Pd/C. The reaction is carried out between $-10°$ C. and $110°$ C., preferably between $0°$ C. and $60°$ C. The reaction can also be carried out in one pot. It can also be performed in protic solvents such as MeOH or water in presence of a picoline-borane complex (*Tetrahedron* (2004), 60, 7899-7906).

General Reaction Technique 3: Alkylation:

The amine derivative is reacted with a compound of formula $G-CH_2X$, wherein X represents Ms-O—, Tf-O—, Ts-O—, Cl, Br or I, or an allyl halogenide in presence of an inorganic base such as $K_2CO_3$ or an org. base such as TEA in a solvent such as THF between $0°$ C. and $+80°$ C. Further details can be found in *Comprehensive Organic Transformations. A guide to Functional Group Preparations*, 2nd Edition, R. C. Larock, Wiley-VC; New York, Chichester, Weinheim, Brisbane, Singapore, Toronto, (1999). Section Amines p. 779.

General Reaction Technique 4: Reduction of an Ester into its Corresponding Alcohol:

An ester can be reduced into its corresponding alcohol using a variety of reducing agents as reviewed by R. C. Larock in *Comprehensive Organic Transformations A guide to Functional Group Preparations*, 2nd Ed., Wiley, New York, Chichester, Weinheim, Brisbane, Singapore, Toronto (1999), Section Alcohols and phenols; p. 1114 to 1120. Among them $LiAlH_4$ or DIBAH are the most preferred.

General Reaction Technique 5: Amino Deprotection:

The benzyl carbamates are deprotected by hydrogenolysis over a noble catalyst (e.g. Pd/C or $Pd(OH)_2/C$). The Boc group is removed under acidic conditions such as HCl in an organic solvent such as MeOH or dioxane, or TFA neat or diluted in a solvent such as DCM. Further general methods to remove amine protecting groups have been described in *Protecting Groups in Organic Synthesis*, 3rd Ed (1999), 494-653; T. W. Greene, P. G. M. Wuts (Publisher: John Wiley and Sons, Inc., New York, N.Y.).

General Reaction Technique 6: Reduction of Aldehydes into their Corresponding Alcohols:

The aldehydes can be reduced to the corresponding alcohols using a variety of reducing agents as reviewed by Larock, R. C. in *Comprehensive Organic Transformations A guide to Functional Group Preparations*, 2nd Ed., Wiley, New York, Chichester, Weinheim, Brisbane, Singapore, Toronto (1999), Section Alcohols and phenols; p. 1075 to 1110. Among them $LiAlH_4$ and $NaBH_4$ are the most preferred.

General Reaction Technique 7: Alcohol Activation:

The alcohol is reacted with Ms-Cl, Tf-Cl or Ts-Cl in presence of a base such as TEA in a dry aprotic solvent such as pyridine, THF or DCM between $-30°$ C. and $+50°$ C. In the case of the trifluoromethanesulfonate or methanesulfonate, $Tf_2O$ or $Ms_2O$ can also be used. These sulfonates can be reacted with NaI in acetone between $+40°$ C. and $+80°$ C. delivering the corresponding iodo derivatives.

General Reaction Technique 8: Oxidation of an Alcohol into an Aldehyde:

The alcohols can be transformed into their corresponding aldehydes through oxidation under Swern (see D. Swern et al., *J. Org. Chem.* (1978), 43, 2480-2482) or Dess Martin (see D. B. Dess and J. C. Martin, *J. Org. Chem.* (1983), 48, 4155) conditions, respectively Alternatively the esters can be transformed into their corresponding aldehydes by controlled reduction with a bulky hydride reagent such as DIBAH.

General Preparation Methods:

The compounds of formula (I) can be manufactured by the methods given below, by the methods given in the examples or by analogous methods. Optimum reaction conditions may vary with the particular reactants or solvents used, but such conditions can be determined by a person skilled in the art by routine optimisation procedures.

Sections a) to e) hereafter describe general methods for preparing compounds of formula (I). The preparation of elaborated intermediates and basic building blocks is described thereafter. General synthetic methods used repeatedly throughout the schemes below are referenced to and described in the end of this section. If not indicated otherwise, the generic groups U, W, $R^1$, A, B and G are as defined for formula (I).

a) The compounds of formula (I) can be obtained by deprotecting a compound of formula II

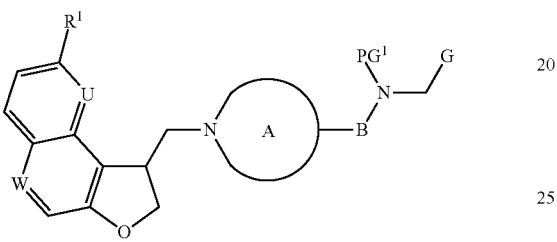

wherein $PG^1$ is an amino protecting group such as Cbz or Boc following general reaction technique 5.

b) The compounds of formula (I) can be obtained by reacting a compound of formula III

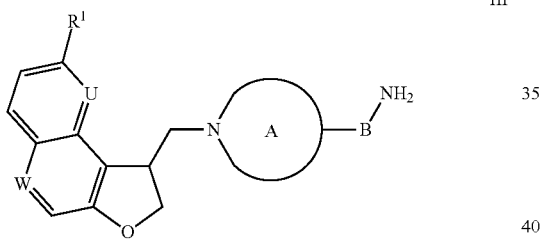

with an aldehyde of formula G-CHO following general reaction technique 2 or with a derivative of formula $G\text{-}CH_2\text{-}X$ wherein X is halogen or Ms-O—, Tf-O— or Ts-O— following general reaction technique 3.

c) The compounds of formula (I) can be obtained by ring closing a compound of formula IV

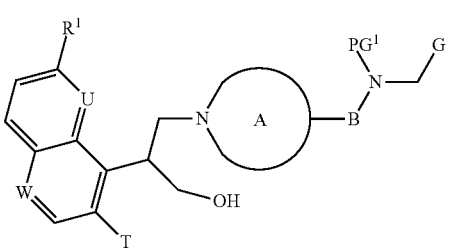

wherein T represents a halogen such as fluorine and $PG^1$ an amino protecting group such as Cbz or Boc. In case T=F, the ring closure is carried out using a base such as t-BuOK; in case T=Cl a palladium catalyzed etherification reaction is used, as described in *J. Am. Chem. Soc.* (2001), 123, 12202. The amino protecting group $PG^1$ is removed following general reaction technique 5.

d) The compounds of formula (I) can be obtained by reacting a compound of formula V

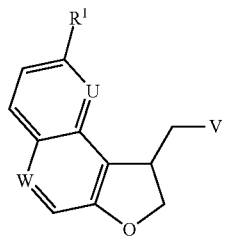

wherein V is halogen or Ms-O—, Tf-O— or Ts-O—, with a compound of formula VI

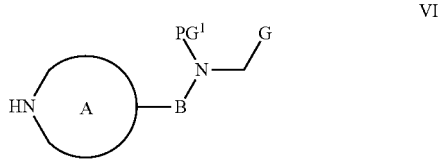

wherein $PG^1$ represents an amino protecting group such as Cbz or Boc as described in general reaction technique 3 and followed by removal of the amino protecting group $PG^1$ following general reaction technique 5.

e) The compounds of formula (I) can be obtained by reacting a compound of formula VII

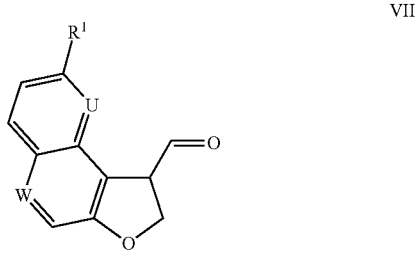

with a compound of formula VI under reductive amination conditions as described in General reaction technique 2 and followed by removal of the amino protecting group $PG^1$ following general reaction technique 5.

Whenever the compounds of formula (I) are obtained in the form of mixtures of enantiomers, the enantiomers can be separated using methods known to one skilled in the art: e.g. by formation and separation of diastereomeric salts or by HPLC over a chiral stationary phase such as a Regis Whelk-O1(R,R) (10 µm) column, a Daicel ChiralCel OD-H (5-10 µm) column, or a Daicel ChiralPak IA (10 µm) or AD-H (5 µm) column. Typical conditions of chiral HPLC are an isocratic mixture of eluent A (EtOH, in presence or absence of an amine such as TEA, diethylamine) and eluent B (Hex), at a flow rate of 0.8 to 150 mL/min.

The compounds of formula (I) obtained according to the above-mentioned general preparation methods may then, if desired, be converted into their salts, and notably into their pharmaceutically acceptable salts.

Preparation of Compounds of Formula II to VII

The compounds of formula II and IV can be prepared as described in Scheme 1 hereafter.

Scheme 1

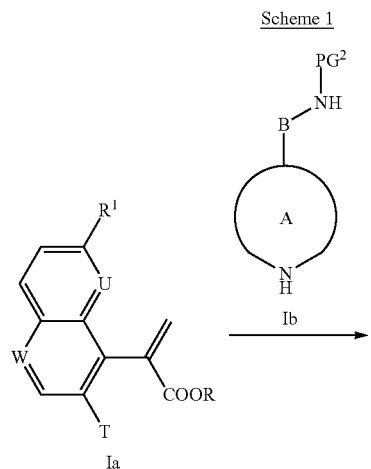

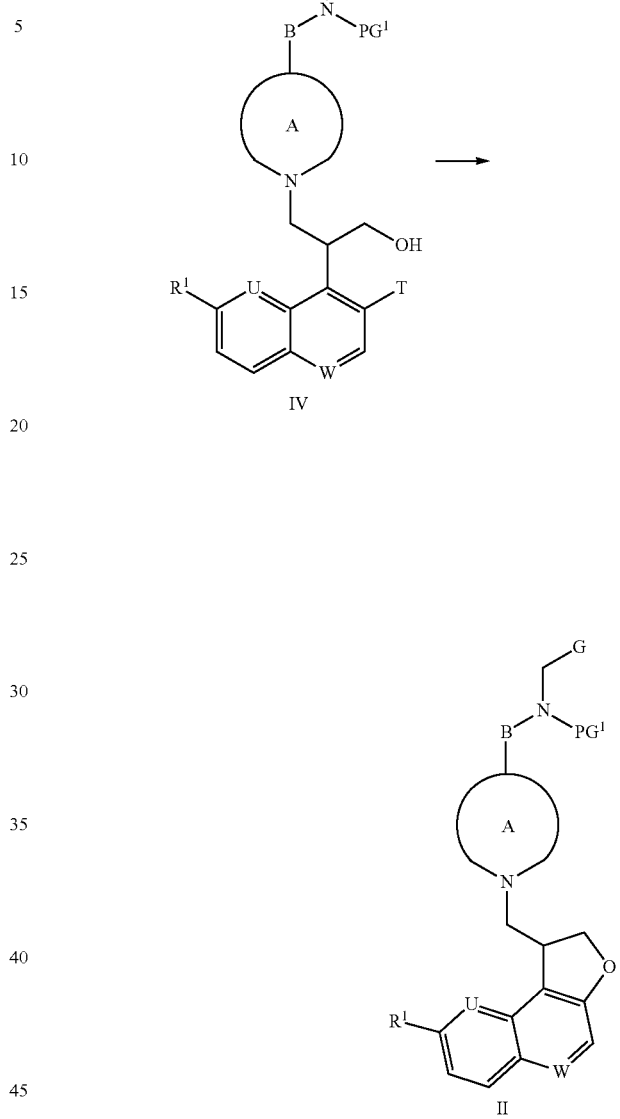

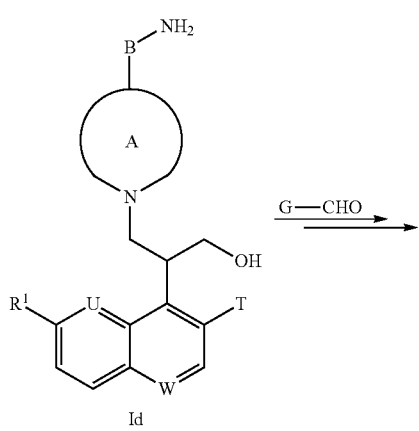

In Scheme 1, R represents alkyl, $PG^1$ and $PG^2$ represent independently from each other an amino protecting group such as Cbz or Boc.

The acrylic derivatives of formula Ia can be reacted with the alicyclic amine derivatives of formula Ib and reduced into the corresponding alcohols following general reaction technique 4, affording the intermediates of formula Ic. The amino protecting group can be removed following general reaction technique 5. The resulting primary amines of formula Id can be reacted with the aldehydes of formula G-CHO under reductive amination conditions following general reaction technique 2 and the intermediate secondary amines can be protected following general reaction technique 1, affording the compounds of formula IV. The compounds of formula II can be obtained as described in section c) above.

The compounds of formula III can be prepared as described in Scheme 2 hereafter.

Scheme 2

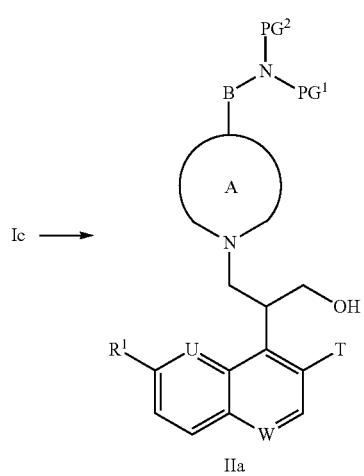

In Scheme 2, $PG^1$ and $PG^2$ represent independently from each other an amino protecting group such as benzyl, Cbz or Boc.

The intermediates of formula Ic can be protected uing general reaction technique 1 and the intermediates of formula IIa can be ring closed as described in section c) above. The protecting groups on the compounds of formula IIb can then be removed following general reaction technique 5.

The compounds of formula V and VII can be obtained as described in Scheme 3 hereafter.

Scheme 3

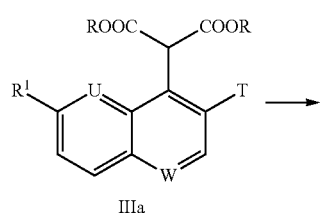

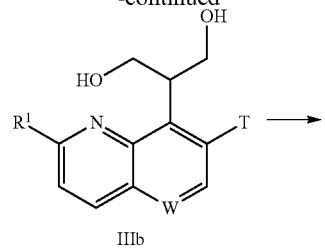

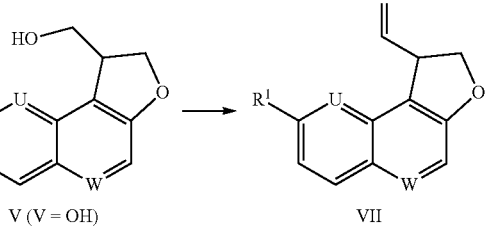

In Scheme 3, R represents alkyl.

The intermediates of formula IIIa can be reduced to the corresponding diols of formula IIIb following general reaction technique 4 and cyclised in presence of a strong base such as t-BuOK as described above. The compounds of formula V wherein V is halogen, —O-Ms, —O-Tf or —O-Ts can be obtained from derivatives of formula V wherein V is OH following general reaction technique 7. The compounds of formula VII can be obtained by oxidation of the alcohols of formula V following general reaction technique 8.

The compounds of formula VI can be obtained as described in Scheme 4 hereafter.

Scheme 4

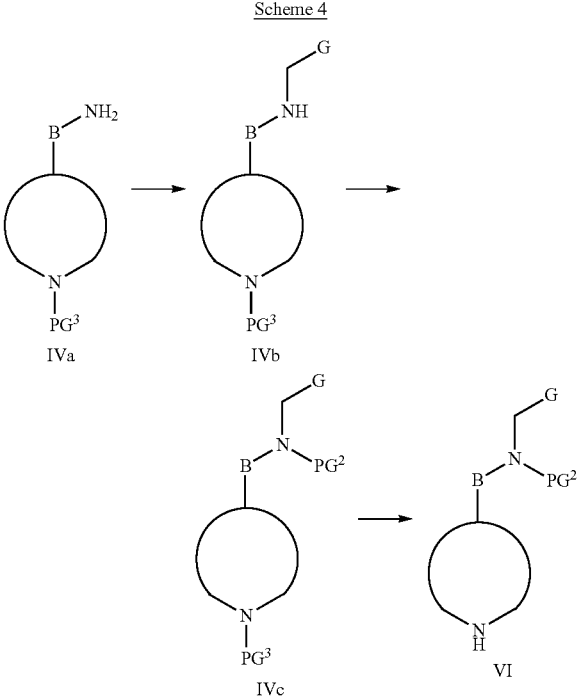

In Scheme 4, $PG^2$ and $PG^3$ represent an amino protecting group such as benzyl, Cbz or Boc.

The commercially available amines of formula IVa (e.g. 2-aminomethylmorpholine-4-carboxylic acid tent-butyl ester, 3-aminomethylpiperidine-1-carboxylic acid tert-butyl ester, 3-aminomethyl-pyrrolidine-1-carboxylic acid tert-butyl ester or 4-aminopiperidine-1-carboxylic acid tent-butyl ester) may be transformed into the corresponding secondary amine derivatives of formula IVb following general reaction technique 2 and protected following general reaction technique 1. The amino protecting group on the alicyclic ring can then be removed following general reaction technique 5, affording the compounds of formula VI.

Preparation of the Starting Compounds

The compounds of formula Ia can be obtained as described in WO 2007/122258, WO 2004/058144 and WO 2007/081597.

The compounds of formula Ib wherein ring A represents the group $A^1$, $R^2$ represents H, B is absent, and $PG^2$ is either Cbz or Boc are commercially available, as well as the compound of formula Ib wherein ring A represents the group $A^1$, $R^2$ represents F, B is absent, and $PG^2$ is Cbz. The compounds of formula Ib wherein ring A represents the group $A^2$ or $A^3$, $R^2$ represents H, B is absent, and $PG^2$ is Boc are also commercially available. The compounds of formula Ib wherein A represents a pyrrolidin-1,3-diyl, a piperidin-1,3-diyl or a morpholin-2,4-diyl group, B represents $CH_2$, and $PG^2$ is either Cbz or Boc are commercially available ($PG^2$=Boc), or can be synthesized according to or in analogy to the procedures given in the experimental part below or in analogy.

The compound of formula Ib wherein ring A represents the group $A^1$, $R^2$ represents $CH_2OH$, B is absent and $PG^2$ is Cbz can be prepared as shown in Scheme 5 hereafter.

Scheme 5

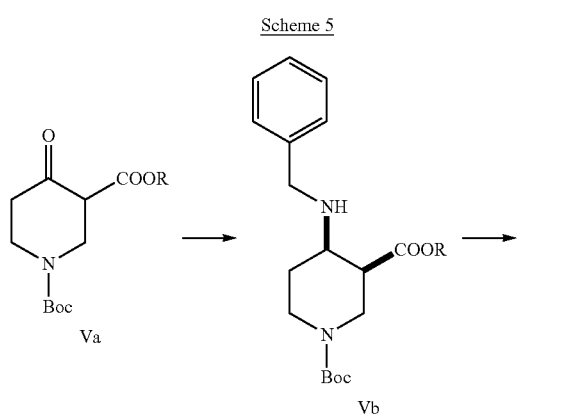

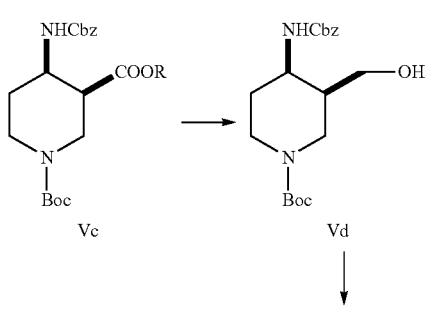

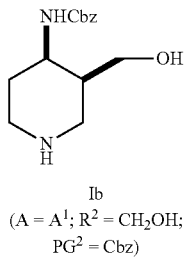

Ib
($A = A^1$; $R^2 = CH_2OH$; $PG^2 = Cbz$)

The commercially available compounds of formula Va were reacted with benzylamine affording the intermediate enamine which was hydrogenated over a Pd/C affording the derivatives of formula Vb. The benzyl protecting group was removed after reduction over platinum and the free amine was protected as a Cbz group. The intermediates of formula Vc were transformed into the corresponding alcohol of formula Vd following general reaction technique 4. The intermediate alcohol of formula Vd was transformed into the derivatives of formulae IBa and Ib by selective deprotection of the amino protecting group following general reaction technique 5. If required the free alcohol function can transiently be protected by formation of a silylether (e.g by reaction with TBDMS-Cl or TBDPS-Cl in presence of a base such as imidazole or TEA) and later on deprotected (e.g treatment with HF, or TBAF).

The compounds of formula ilia can be obtained according to or in analogy to WO 2007/122258.

The compound of formula IVa wherein ring A represents the group $A^1$, $R^2$ represents $CH_2OH$, B is absent and $PG^3$ is Boc can be prepared by deprotection of the compound of formula Vd using general reaction technique 5.

The compounds of formula G-CHO are commercially available or can be prepared as described in WO 02/056882 (e.g. structures wherein $Y^1$=CH and $Y^2$=N or structures wherein Z=CH and Q=S or structures wherein Z=N and Q=S or O). (2E)-3-(2,5-difluorophenyl)-2-propenal was prepared according to WO 2006/010831.

The compounds of formula G-$CH_2$X wherein X is —O-Ms, —O-Tf or —O-Ts can be obtained by reduction of the compounds of formula G-CHO following general reaction technique 6 and activation of the primary alcohol following general reaction technique 7. The compounds of formula G-$CH_2$X wherein X is halogen can be obtained by reaction of the corresponding compounds wherein X is —O-Ms, —O-Tf or —O-Ts with the desired sodium or potassium halide such as NaI in a solvent such as acetone between 40° C. and 70° C.

Particular embodiments of the invention are described in the following examples, which serve to illustrate the invention in more detail without limiting its scope in any way.

EXAMPLES

All temperatures are stated in ° C. Compounds are characterized by $^1$H-NMR (300 MHz) (Varian Oxford); or by $^1$H-NMR (400 MHz) (Bruker Advance 400). Chemical shifts are given in ppm relative to the solvent used; multiplicities: s=singlet, d=doublet, t=triplet, q=quadruplet, p=pentuplet, hex=hexet, hept=heptet, m=multiplet, br.=broad, app.=apparent coupling constants are given in Hz. Alternatively compounds are characterized by LC-MS (Sciex API 2000 with Agilent 1100 Binary Pump and DAD, using RP-C18 based columns); by TLC (TLC-plates from Merck, Silica gel 60 $F_{254}$); or by melting point. Compounds are purified by chromatography on Silica gel 60A. $NH_4OH$ as used for CC is 25% aq. Racemates can be separated into their enantiomers as described before. Preferred conditions of chiral HPLC are: ChiralPak AD (4.6×250 mm, 5 µm) column, using an isocratic mixture (eg. at a ratio of 10/90) of eluent A (EtOH, in presence of diethylamine in an amount of eg. 0.1%) and eluent B (Hex), at rt, at a flow rate of eg. 0.8 mL/min.

Example 1 rac-[(E)-3-(2,5-difluoro-phenyl)-allyl]-[1-(2-methoxy-8,9-dihydro-furo[2,3-h]quinolin-9-ylmethyl)-piperidin-4-yl]-amine 1.i. rac-3-(4-amino-piperidin-1-yl)-2-(7-fluoro-2-methoxy-quinolin-8-yl)-propan-1-ol A solution of rac-{1-[2-(7-fluoro-2-methoxy-quinolin-8-yl)-3-hydroxy-propyl]-piperidin-4-yl}-carbamic acid tert-butyl ester (WO 2007/081597, 1.42 g, 3.28 mmol) in a mixture of TFA (15 mL) and DCM (9 mL) was stirred at rt for 20 min. The solvent was removed in vacuo and the residue was diluted in sat. $NaHCO_3$ (20 mL). The pH was adjusted to 12 adding 6M NaOH. The aq. layer was extracted 3 times with DCM-MeOH (9-1, 3×25 mL). The combined org. layers were washed once with brine (20 mL), dried over $Na_2SO_4$, filtered and concentrated to dryness to afford the title amine as a yellowish gum (1.1 g, 100% yield).

$^1$H NMR (d6-DMSO) δ: 8.22 (d, J=9.0 Hz, 1H); 7.78 (dd, J=6.0, 9.0 Hz, 1H); 7.25 (dd, J=9.0, 10.5 Hz, 1H); 6.97 (d, J=9.0 Hz, 1H); 4.79 (br. s, 1H); 4.27 (br. s, 1H); 4.03 (overlapped m, 1H); 3.99 (s, 3H); 3.83 (m, 1H); 2.70-3.00 (m, 4H); 2.43 (m, 1H); 1.86-1.98 (m, 2H); 1.54-1.64 (m, 2H); 1.26-1.48 (m, 2H); 0.98-1.16 (m, 2H).

MS (ESI, m/z): 334.3 [M+J$^+$].

1.ii. rac-3-{4-[(E)-3-(2,5-difluoro-phenyl)-allylamino]-piperidin-1-yl}-2-(7-fluoro-2-methoxy-quinolin-8-yl)-propan-1-ol To a solution of intermediate 1.i (0.46 g, 1.39 mmol) in MeOH (7 mL) and DCE (24 mL) were added 3 Å molecular sieves (4 g) and (E)-3-(2,5-difluoro-phenyl)-propenal (WO 2006/010831; 0.23 g, 1.39 mmol, 1 eq.). The mixture was stirred at 50° C. overnight. The reaction mixture was cooled to 0° C. and $NaBH_4$ (0.44 g, 11.5 mmol) was added. The reaction proceeded for 40 min at this temperature. The reaction mixture was diluted with DCM-MeOH (9:1, 30 mL), filtered and the solid was washed with DCM (20 mL). The filtrate was washed with sat. $NaHCO_3$ (10 mL) and the aq. layer was extracted three times with DCM-MeOH (3×10 mL). The org. layer was dried over $Na_2SO_4$, filtered and concentrated to dryness. The residue was purified by CC (DCM-MeOH 93:7 containing 0.7% of aq. $NH_4OH$) to afford the title compound as a white foam (0.56 g, 83% yield).

$^1$H NMR (d6-DMSO) δ: 8.22 (d, J=9.0 Hz, 1H); 7.78 (dd, J=6.0, 9.0 Hz, 1H); 7.43 (ddd, J=3.3, 6.3, 9.6 Hz, 1H); 7.25 (dd, J=9.0, 10.5 Hz, 1H); 7.20 (overlapped m, 1H); 7.08 (m, 1H); 6.97 (d, J=9.0 Hz, 1H); 6.57 (d, J=15.9 Hz, 1H); 6.46 (td, J=5.4, 15.9 Hz, 1H); 4.79 (br. s, 1H); 4.28 (br. s, 1H); 4.01 (overlapped m, 1H); 3.99 (s, 3H); 3.84 (m, 1H); 3.32 (br. s, 2H); 2.70-3.00 (m 4H); 2.34 (m, 1H); 1.88-2.00 (m, 2H); 1.68-1.78 (m, 2H); 1.66 (br. s, 1H); 1.04-1.20 (m, 2H).

MS (ESI, m/z): 486.3 [M+H$^+$].

1.iii. rac-[(E)-3-(2,5-difluoro-phenyl)-allyl]-{1-[2-(7-fluoro-2-methoxy-quinolin-8-yl)-3-hydroxy-propyl]-piperidin-4-yl}-carbamic acid tert-butyl ester To a solution of intermediate 1.ii (0.55 g, 1.26 mmol) in DCM (36 mL) was added $Boc_2O$ (0.49 g, 2.26 mmol, 2 eq.). The mixture was stirred at rt for 3 h. The crude mixture was directly subjected to CC (DCM-MeOH 98:2 to 97:3) to afford the title compound as a beige foam (0.664 g, 86% yield).

MS (ESI, m/z): 586.3 [M+H$^+$].

1.iv. rac-[(E)-3-(2,5-difluoro-phenyl)-allyl]-[1-(2-methoxy-8,9-dihydro-furo[2,3-h]quinolin-9-ylmethyl)-piperidin-4-yl]-carbamic acid tert-butyl ester To a solution of intermediate 1.iii (0.1 g, 0.17 mmol) in THF (1 mL) was added t-BuOK (0.084 g, 4.2 eq.). The mixture was stirred at 70° C. for 1 h. Water was added (5 mL) and the mixture was extracted with EA (2×10 mL). The combined org. layers were dried over $Na_2SO_4$ and concentrated. The residue was purified by CC (DCM-MeOH 49:1 containing 0.2% of aq.$NH_4OH$) to afford the title compound as a yellow oil (0.030 g, 31% yield).

MS (ESI, m/z): 566.1 [M+H$^+$].

1.v. rac-[(E)-3-(2,5-difluoro-phenyl)-allyl]-[1-(2-methoxy-8,9-dihydro-furo[2,3-h]quinolin-9-ylmethyl)-piperidin-4-yl]-amine Starting from intermediate 1.iv (0.025 g, 0.043 mmol), the title compound was obtained as a colourless oil (0.011 g, 55% yield) using the procedure described in step 1.i. The crude material was purified by CC (DCM-MeOH 19:1 containing 0.5% of aq. $NH_4OH$).

$^1$H NMR (d6-DMSO) δ: 8.12 (d, J=9.0 Hz, 1H); 7.66 (d, J=8.7 Hz, 1H); 7.46 (ddd, J=3.3, 6.3, 9.6 Hz, 1H); 7.23 (m, 1H); 7.09 (m, 1H); 6.99 (d, J=9.0 Hz, 1H); 6.76 (d, J=8.7 Hz, 1H); 6.61 (d, J=16.5 Hz, 1H); 6.51 (td, J=5.4, 16.5 Hz, 1H); 4.71 (app. t, J=9.0 Hz, 1H); 4.51 (dd, J=5.1, 9.0 Hz, 1H); 4.06 (m, 1H); 3.95 (s, 3H); 3.35 (br. d, J=4.8 Hz, 2H); 3.15 (m, 1H) 3.10 (overlapped m, 1H); 2.72 (m,1H); 2.46-2.35 (m, 2H); 213 (m, 1H); 1.95 (m, 1H); 1.72-1.90 (m, 3H); 1.18-1.34 (m, 2H).

MS (ESI, m/z): 466.3 [M+H$^+$].

Example 2 rac-(2,3-dihydro-[1,4]dioxino[2,3-c]pyridin-7-ylmethyl)-[1-(2-methoxy-8,9-dihydro-furo[2,3-h]quinolin-9-ylmethyl)-piperidin-4-yl]-amine Starting from intermediate 1.i (0.290 g, 0.870 mmol) and 2,3-dihydro-[1,4]dioxino[2,3-c]pyridine-7-carbaldehyde (commercially available, 0.150 g, 1.05 eq.), the title compound was obtained as a white foam (0.16 g) using the procedures described in Example 1, steps 1.ii (reductive amination, 67% yield), 1.iii (N-Boc formation, 89% yield), 1.iv (cyclization, 83% yield) and 1.v (Boc deprotection, 81% yield). The crude reaction mixtures were purified by CC using DCM-MeOH-aq. $NH_4OH$ (19:1:0.1 to 9:1:0.1) as eluent.

$^1$H NMR (d6-DMSO) δ: 8.11 (d, J=9.0 Hz, 1H); 8.00 (s, 1H); 7.67 (d, J=8.7 Hz, 1H); 6.98 (d, J=8.7 Hz, 1H); 6.94 (s, 1H); 6.77 (d, J=9.0 Hz, 1H); 4.72 (t, J=9.0 Hz, 1H); 4.59 (dd, J=5.1, 9.0 Hz, 1H); 4.25-4.35 (m, 4H); 4.06 (m, 1H); 3.96 (s, 3H); 3.67 (s, 2H); 3.16 (dd, J=3.0, 11.7 Hz, 1H); 3.10 (overlapped m, 1H); 2.72 (m, 1H); 2.36-2.46 (m, 2H); 2.10-2.22 (m, 2H); 1.94 (m, 1H); 1.72-1.88 (m, 2H); 1.22-1.38 (m, 2H)

MS (ESI, m/z): 466.0 [M+H$^+$]..

Example 3 rac-(6,7-dihydro-[1,4]dioxino[2,3-c]pyridazin-3-ylmethyl)-[1-(2-methoxy-8,9-dihydro-furo[2,3-h]quinolin-9-ylmethyl)-piperidin-4-yl]-amine

3.i. rac-benzyl-[1-(2-methoxy-8,9-dihydro-furo[2,3-h]quinolin-9-ylmethyl)-piperidin-4-yl]-amine Starting from intermediate 1.i (0.852 g, 2.55 mmol) and benzaldehyde (0.256 mL, 1 eq.), the title compound was obtained as a yellowish oil (0.805 g) using the procedures described in Example 1, steps 1.ii (reductive amination, 86% yield), 1.iii (N-Boc formation, 94% yield), 1.iv (cyclization, 97% yield) and 1.v (Boc deprotection, 100% yield). The crude reaction mixtures were purified by CC using DCM-MeOH-aq. NH$_4$OH (19:1:0.1 to 9:1:0.1) as eluent.

MS (ESI, m/z): 404.2 [M+H$^+$].

3.ii. rac-1-(2-methoxy-8,9-dihydro-furo[2,3-h]quinolin-9-ylmethyl)-piperidin-4-ylamine To a solution of intermediate 3.i (0.8 g, 1.98 mmol) in MeOH (30 mL) was added 10% Pd/C (0.8 g). The mixture was evacuated twice and backfilled with nitrogen and then with hydrogen. The reaction was stirred at 40° C. for 2 h. The reaction mixture was cooled to rt and diluted with EA (100 mL). The catalyst was removed by filtration and washed with EA. The filtrate was concentrated to dryness. The residue was purified by CC (DCM-MeOH 9:1 containing 1% aq. NH$_4$OH then DCM-MeOH 6:1 containing 1% aq. NH$_4$OH) to afford the title amine as a yellowish oil (0.48 g, 77% yield).

MS (ESI, m/z): 314.2 [M+H$^+$].

3.iii. rac-(6,7-dihydro-[1,4]dioxino[2,3-c]pyridazin-3-ylmethyl)-[1-(2-methoxy-8,9-dihydro-furo[2,3-h]quinolin-9-ylmethyl)-piperidin-4-yl]-amine Starting from intermediate 3.ii (0.065 g, 0.207 mmol) and 6,7-dihydro-[1,4]dioxino[2,3-c]pyridazine-3-carbaldehyde (WO 2007/071936; 0.034 g, 1 eq.), the title compound was obtained as a white foam (0.037 g, 37% yield) using the procedure of Example 1, step 1.ii. The crude mixture was purified by CC (DCM-MeOH 9:1 containing 1% aq. NH$_4$OH).

$^1$H NMR (d6-DMSO) δ: 8.11 (d, J=8.9 Hz, 1H); 7.67 (d, J=8.7 Hz, 1H); 7.17 (s, 1H); 6.98 (d, J=8.7 Hz, 1H); 6.76 (d, J=8.9 Hz, 1H); 4.72 (t, J=9.0 Hz, 1H); 4.59 (dd, J=2.9, 9.0 Hz, 1H); 4.45-4.49 (m, 2H); 4.34-4.38 (m, 2H); 4.06 (m, 1H); 3.95 (s, 3H); 3.84 (s, 2H); 3.16 (dd, J=3.0, 12.0 Hz, 1H); 3.10 (overlapped m, 1H); 2.73 (m, 1H); 2.30-2.45 (m, 3H); 2.09 (m, 1H); 1.93 (m, 1H); 1.71-1.88 (m, 2H); 1.20-1.38 (m, 2H).

MS (ESI, m/z): 464.3 [M+H$^+$].

Example 4 rac-6-{[1-(2-methoxy-8,9-dihydro-furo[2,3-h]quinolin-9-ylmethyl)-piperidin-4-ylamino]-methyl}-4H-pyrido[3,2-b][1,4]thiazin-3-one

4.i. 6-hydroxymethyl-4H-pyrido[3,2-b][1,4]thiazin-3-one

To a suspension of 3-oxo-3,4-dihydro-2H-pyrido[3,2-b][1,4]thiazine-6-carboxylic acid methyl ester (WO 02/056882; 36.0 g, 161 mmol) in THF (240 mL) was added a solution of lithium triethylborohydride in THF (1M, 430 g, 3 eq.) at 5-10° C. over 70 min. Acetic acid (87 g, 9 eq.) was added dropwise at 10-25° C. to the brown solution. MeOH (180 mL) was added to the suspension at 20° C. The reaction vessel was then constantly cooled externally at 21-37° C. while a 5% w/w hydrogen peroxide solution (300 mL, 3 eq.) was added over 35 min, and a 10% w/w hydrogen peroxide solution (300 mL, 6 eq.) was added over further 35 min. A sat. aq sodium metabisulfite solution (147 g) was added at 24-36° C. The reaction mixture was concentrated under reduced pressure at 50° C. whereupon the product started to crystallize. MeOH was added to the suspension in three portions (3×180 mL) followed by removal of ca. 180 mL of solvent under reduced pressure after each addition. The solid was filtered, washed with water (2×150 mL) and tert-butyl methyl ether (150 ml). To the wet cake was added toluene in two portions (2×50 mL) followed by the removal of 50 mL solvent under reduced pressure at 50° C. The title compound was obtained as a light yellow solid (22.86 g, 73% yield; m.p. 120-135° C.).

$^1$H-NMR (d$_6$-DMSO): δ 10.86 (s, 1H), 7.77 (d, J=7.8 Hz, 1H), 7.11 (d, J=7.8 Hz, 1H), 5.43 (br. s, 1H), 4.47 (s, 2H), 3.53 (s, 2H).

4.ii. 3-oxo-3,4-dihydro-2H-pyrido[3,2-b][1,4]thiazine-6-carbaldehyde

To a solution of intermediate 4.i (15.9 g, 81.02 mmol) in DCM (1 L) and THF (1 L) was added manganese dioxide (50 g). After 2 h, more manganese dioxide (50 g) was added. The reaction proceeded further 6 h. The reaction mixture was filtered through a pad of celite. The cake was further washed with DCM-THF mixture (1:1, 800 mL), and the filtrate was concentrated to dryness. The residue was triturated with Hept (500 mL) and the solid was filtered off and dried under high vacuum to leave the title aldehyde as a beige solid (9.85 g, 62% yield).

$^{13}$C NMR (d6-DMSO) δ: 192.51, 166.27, 150.16, 148.99, 136.81, 123.29, 117.67, 28.80.

4.iii. rac-6-{[1-(2-methoxy-8,9-dihydro-furo[2,3-h]quinolin-9-ylmethyl)-piperidin-4-ylamino]-methyl}-4H-pyrido[3,2-b][1,4]thiazin-3-one Starting from intermediate 3.ii (0.090 g, 0.287 mmol) and intermediate 4.ii (0.059 g, 1 eq.), the title compound was obtained as a white foam (0.095 g, 67% yield) using the procedure of Example 1, step 1.ii. The crude mixture was purified by CC (DCM-MeOH 9:1 containing 1% aq. NH$_4$OH).

$^1$H NMR (d6-DMSO) δ: 10.83 (s, 1H); 8.11 (d, J=9.0 Hz, 1H); 7.72 (d, J=7.8 Hz, 1H); 7.67 (d, J=8.7 Hz, 1H); 7.30 (d, J=7.8 Hz, 1H); 6.98 (d, J=8.7 Hz, 1H); 6.77 (d, J=9.0 Hz, 1H); 4.72 (t, J=9.0 Hz, 1H); 4.58 (overlapped dd, J=5.1, 9.0 Hz, 1H); 4.08 (m, 1H); 3.96 (s, 3H); 3.72 (s, 2H); 3.52 (s, 2H); 3.15 (dd, J=3.0, 11.7 Hz, 1H); 3.11 (overlapped m, 1H); 2.73 (m, 1H); 2.36-2.44 (m, 2H); 2.20 (m, 1H); 2.13 (m, 1H); 1.94 (m, 1H); 1.74-1.88 (m, 2H); 1.20-1.40 (m, 2H).

MS (ESI, m/z): 492.1 [M+H$^+$].

Example 5 rac-6-{[1-(2-methoxy-8,9-dihydro-furo[2,3-h]quinolin-9-ylmethyl)-piperidin-4-ylamino]-methyl}-4H-pyrido[3,2-b][1,4]oxazin-3-one Starting from intermediate 3.ii (0.090 g, 0.287 mmol) and 3-oxo-3,4-dihydro-2H-pyrido[3,2-b][1,4]oxazine-6-carbaldehyde (WO 02/056882; 0.059 g, 1.05 eq.), the title compound was obtained as a white foam (0.081 g, 54% yield) using the procedure of Example 1, step 1.ii. The crude mixture was purified by CC (DCM-MeOH 93:7 containing 0.7% aq. NH$_4$OH).

$^1$H NMR (d6-DMSO) δ: 11.13 (s, 1H); 8.11 (d, J=9.0 Hz, 1H); 7.67 (d, J=8.7 Hz, 1H); 7.28 (d, J=8.1 Hz, 1H); 7.01 (d, J=8.1 Hz, 1H); 6.98 (d, J=8.7 Hz, 1H); 6.77 (d, J=9.0 Hz, 1H); 4.72 (t, J=8.7 Hz, 1H); 4.60 (s, 2H); 4.59 (overlapped dd, J=5.1, 8.7 Hz, 1H); 4.06 (m, 1H); 3.96 (s, 3H); 3.69 (s, 2H); 3.15 (dd, J=3.3, 12.6 Hz, 1H); 3.11 (overlapped m, 1H); 2.72 (m, 1H); 2.36-2.46 (m, 2H); 2.13 (m, 1H); 2.06 (br. s, 1H); 1.94 (m, 1H); 1.74-1.88 (m, 2H); 1.20-1.40 (m, 2H).

MS (ESI, m/z): 476.2 [M+H$^+$].

Example 6 rac-6-{[1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one 6.i. rac-1-(8-methoxy-1,2-dihydro-3-oxa-5,9-diaza-cyclopenta[a]naphthalen-1-ylmethyl)-piperidin-4-ylamine Starting from rac-{1-[2-(3-fluoro-6-methoxy-[1,5]naphthyridin-4-yl)-3-hydroxy-propyl]-piperidin-4-yl}-carbamic acid tert-butyl ester (WO 2004/58144; 2.60 g, 5.98 mmol), the title amine (0.4 g) was obtained as a off-white foam using the procedures described in Example 1, step 1.i (Boc deprotection, 97% yield) and Example 3, steps 3.i (reductive amination, 71% yield; N-Boc formation, 96% yield; cyclization with 1 eq. of t-BuOK at rt, 73% yield; Boc deproction, 80% yield) and 3.ii (hydrogenolysis, 68% yield). The crude mixture was purified by CC using DCM-MeOH-aq. NH$_4$OH (9:1:0.1) as eluent.

MS (ESI, m/z): 315.2 [M+H$^+$].

6. ii. rac-6-{[1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one Starting from intermediate 6.i (0.090 g, 0.286 mmol) and 3-oxo-3,4-dihydro-2H-pyrido[3,2-b][1,4]oxazine-6-carbaldehyde (0.057 g, 1.1 eq.), the title compound was obtained as a white foam (0.088 g, 65% yield) using the procedure of Example 1, step 1.ii. The crude mixture was purified by CC (DCM-MeOH 93:7 containing 0.7% aq. NH$_4$OH).

$^1$H NMR (d6-DMSO) δ: 11.13 (s, 1H); 8.48 (s, 1H); 8.17 (d, J=9.0 Hz, 1H); 7.29 (d, J=8.4 Hz, 1H); 7.03 (d, J=9.0 Hz, 1H); 7.02 (d, J=8.4 Hz, 1H); 4.82 (t, J=9.0 Hz, 1H); 4.66 (overlapped dd, J=6.0, 9.0 Hz, 1H); 4.60 (s, 2H); 4.16 (m, 1H); 3.99 (s, 3H); 3.69 (s, 2H); 3.18 (dd, J=3.6, 12.0 Hz, 1H); 3.07 (overlapped m, 1H); 2.72 (m, 1H); 2.55 (overlapped m, 1H); 2.40 (m, 1H); 2.14 (m, 1H); 2.08 (br. s, 1H); 1.95 (m, 1H); 1.72-1.88 (m, 2H); 1.20-1.40 (m, 2H).

MS (ESI, m/z): 477.0 [M+H$^+$].

Example 7 rac-6-{[1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one Starting from intermediate 6.i (0.090 g, 0.287 mmol) and 3-oxo-3,4-dihydro-2H-pyrido[3,2-b][1,4]thiazine-6-carbaldehyde (0.061 g, 1.1 eq.), the title compound was obtained as an off-white foam (0.080 g, 57% yield) using the procedure of Example 1, steps 1.ii. The crude mixture was purified by CC (DCM-MeOH 93:7 containing 0.7% aq. NH$_4$OH).

$^1$H NMR (d6-DMSO) δ: 10.83 (s, 1H); 8.48 (s, 1H); 8.17 (d, J=9.0 Hz, 1H); 7.71 (d, J=7.8 Hz, 1H); 7.10 (d, J=7.8 Hz, 1H); 7.03 (d, J=9.0 Hz, 1H); 4.82 (t, J=9.0 Hz, 1H); 4.65 (dd, J=6.0, 9.0 Hz, 1H); 4.17 (m, 1H); 3.99 (s, 3H); 3.72 (s, 2H); 3.52 (s, 2H); 3.18 (dd, J=3.3, 12.0 Hz, 1H); 3.07 (m, 1H); 2.73 (m, 1H); 2.50 (overlapped m, 1H); 2.40 (m, 1H); 2.08-2.20 (m, 2H); 1.95 (m, 1H); 1.72-1.88 (m, 2H); 1.21-1.38 (m, 2H).

MS (ESI, m/z): 493.1 [M+H$^+$].

Example 8 rac-(6,7-dihydro-[1,4]dioxino[2,3-c]pyridazin-3-ylmethyl)-[1-(8-methoxy-1,2-dihydro-3-oxa-5,9-diaza-cyclopenta[a]naphthalen-1-ylmethyl) -piperidin-4-yl]-amine Starting from intermediate 6.i (0.030 g, 0.095 mmol) and 6,7-dihydro-[1,4]dioxino[2,3-c]pyridazine-3-carbaldehyde (0.017 g, 1.1 eq.), the title compound was obtained as an off-white foam (0.012 g, 27% yield) using the procedure of Example 1, step 1.ii. The crude mixture was purified by CC (DCM-MeOH 93:7 containing 0.7% aq. NH$_4$OH). The purity of the compound was 80%.

$^1$H NMR (d6-DMSO) δ: 8.45 (s, 1H); 8.16 (d, J=9.0 Hz, 1H); 7.18 (s, 1H); 7.02 (d, J=9.0 Hz, 1H); 4.81 (t, J=9.0 Hz, 1H); 4.65 (dd, J=3.0, 9.0 Hz, 1H); 4.45-4.51 (m, 2H); 4.33-4.40 (m, 2H); 4.16 (m, 1H); 3.99 (s, 3H); 3.83 (s, 2H); 3.17 (dd, J=3.0, 12.0 Hz, 1H); 3.05 (m, 1H); 2.70 (m, 1H); 2.54 (m, 1H); 2.35 (m, 1H); 2.12 (m, 1H); 1.93 (m, 1H); 1.71-1.84 (m, 2H); 1.20-1.38 (m, 3H).

MS (ESI, m/z): 465.3 [M+H$^+$].

Example 9 rac-(2,3-dihydro-[1,4]dioxino[2,3-c]pyridin-7-ylmethyl)-[1-(8-methoxy-1,2-dihydro-3-oxa-5,9-diaza-cyclopenta[a]naphthalen-1-ylmethyl)-piperidin-4-yl]-amine Starting from intermediate 6.i (0.1 g, 0.317 mmol) and 2,3-dihydro-[1,4]dioxino[2,3-c]pyridine-7-carbaldehyde (0.057 g, 1.1 eq.), the title compound was obtained as a white foam (0.090 g, 61% yield) using the procedure of Example 1, step 1.ii. The crude mixture was purified by CC (DCM-MeOH 93:7 containing 0.7% aq. NH$_4$OH).

$^1$H NMR (d6-DMSO) δ: 8.46 (s, 1H); 8.16 (d, J=9.0 Hz, 1H); 7.98 (s, 1H); 7.01 (d, J=9.0 Hz, 1H); 6.92 (s, 1H); 4.81 (t, J=9.0 Hz, 1H); 4.64 (dd, J=5.7, 9.0 Hz, 1H); 4.22-4.34 (m, 4H); 4.15 (m, 1H); 3.98 (s, 3H); 3.65 (s, 2H); 3.17 (dd, J=3.3, 12.6 Hz, 1H); 3.04 (m, 1H); 2.70 (m, 1H); 2.50 (overlapped m, 1H); 2.36 (m, 1H); 2.02-2.18 (m, 2H); 1.94 (m, 1H); 1.70-1.84 (m, 2H); 1.20-1.40 (m, 2H).

MS (ESI, m/z): 464.1 [M+H$^+$].

Example 10 rac-(2,3-dihydro-benzo[1,4]dioxin-6-ylmethyl)-[1-(8-methoxy-1,2-dihydro-3-oxa-5,9-diaza-cyclopenta[a]naphthalen-1-ylmethyl)-piperidin-4-yl]-amine Starting from intermediate 6.i (0.049 g, 0.152 mmol) and 2,3-dihydro-benzo[1,4]dioxino-6-carbaldehyde (0.027 g, 1.1 eq.), the title compound was obtained as an off-white foam (0.043 g, 61% yield) using the procedure of Example 1, step 1.ii. The crude mixture was purified by CC (DCM-MeOH 9:1 containing 1% aq. NH₄OH).

¹H NMR (CDCl₃) δ: 8.45 (s, 1H); 8.13 (d, J=9.0 Hz, 1H); 6.92 (d, J=9.0 Hz, 1H); 6.80-6.86 (m, 3H); 4.77-4.85 (m, 2H); 4.25 (s, 4H); 4.15 (m, 1H); 4.05 (s, 3H); 3.72 (s, 2H); 3.29 (dd, J=3.3, 12.3 Hz, 1H); 3.12 (m, 1H); 2.78 (m, 1H); 2.48-2.60 (m, 2H); 2.25 (m, 1H); 2.07 (m, 1H); 1.84-2.00 (m, 2H); 1.40-1.56 (m, 3H).

MS (ESI, m/z): 463.2 [M+H⁺].

Example 11 rac-(2,3-dihydro-[1,4]dioxino[2,3-b]pyridin-6-ylmethyl)-[1-(2-methoxy-8,9-dihydro-furo[2,3-h]quinolin-9-ylmethyl)-piperidin-4-yl]-amine Starting from intermediate 3.ii (0.092 g, 0.294 mmol) and 2,3-dihydro-[1,4]dioxino[2,3-b]pyridine-6-carbaldehyde (WO 2003/087098; 0.051 g, 1.05 eq.), the title compound (0.035 g) was obtained as a white foam using the procedure of Example 1, step 1.ii. The crude mixture was purified by CC (DCM-MeOH 93:7 containing 0.7% aq. NH₄OH).

¹H NMR (d6-DMSO) δ: 8.09 (d, J=9.0 Hz, 1H); 7.65 (d, J=8.7 Hz, 1H); 7.20 (d, J=8.4 Hz, 1H); 6.97 (d, J=8.7 Hz, 1H); 6.94 (d, J=8.4 Hz, 1H); 6.74 (d, J=9.0 Hz, 1H); 4.71 (t, J=9.0 Hz, 1H); 4.57 (dd, J=5.4, 9.0 Hz, 1H); 4.34-4.38 (m, 2H); 4.18-4.22 (m, 2H); 4.06 (m, 1H); 3.94 (s, 3H); 3.61 (s, 2H); 3.14 (dd, J=3.0, 12.0 Hz, 1H); 3.09 (overlapped m, 1H); 2.71 (m, 1H); 2.34-2.44 (m, 2H); 2.11 (m, 1H); 2.02 (br. s, 1H); 1.92 (m, 1H); 1.72-1.81 (m, 2H); 1.20-1.36 (m, 2H).

MS (ESI, m/z): 463.6 [M+H⁺].

Example 12

(2,3-dihydro-[1,4]dioxino[2,3-c]pyridin-7-ylmethyl)-[(3S)-1-((1RS)-8-methoxy-1,2-dihydro-3-oxa-5,9-diaza-cyclopenta[a]naphthalen-1-ylmethyl)-pyrrolidin-3-ylmethyl]-amine 12.i. 2-(3-fluoro-6-methoxy-[1,5]naphthyridin-4-yl)-acrylic acid ethyl ester Starting from 8-bromo-7-fluoro-2-methoxy-[1,5]naphthyridine (10 g, 38.9 mmol) and diethyl malonate (17.9 mL, 116.7 mmol), the title compound (4.8 g, 17.3 mmol) was prepared as described in WO 2007/122258 for the analogous methyl ester. The purity of the material was around 80%.

¹H NMR (CDCl₃) δ: 8.72 (d, J=0.6 Hz, 1H); 8.18 (d, J=9.0 Hz, 1H); 7.06 (d, J=8.0 Hz, 1H); 6.68 (d, J=1.2 Hz, 1H); 6.04 (app. t, J=1.2 Hz, 1H); 4.21 (q, J=7.1 Hz, 2H); 3.97 (s, 3H); 1.17 (t, J=7.1 Hz, 3H).

MS (ESI, m/z): 277.2 [M+H⁺].

12.ii. (3RS)-3-[(3S)-3-(tert-butoxycarbonylamino-methyl)-pyrrolidin-1-yl]-2-(3-fluoro-6-methoxy-[1,5]naphthyridin-4-yl)-propionic acid ethyl ester To a mixture of intermediate 12.i (80%, 3.4 g, 10 mmol) and (3R)-pyrrolidin-3-ylmethyl-carbamic acid tert-butyl ester (2.0 g, 10 mmol) in DMF (14 mL) was added TMG (0.19 mL, 0.15 eq.). The mixture was heated to 80° C. for 8 h. After cooling, the solvent was removed in vacuo and the residue was purified by CC (DCM-MeOH 97:3 containing 0.3% aq. NH₄OH) to afford the title compound as a colourless foam (3.0 g). The material contained approximately 10% of DMF.

MS (ESI, m/z): 477.0 [M+H⁺].

12.iii. (3S)-{1-[(2RS)-2-(3-fluoro-6-methoxy-[1,5] naphthyridin-4-yl)-3-hydroxy-propyl]-pyrrolidin-3-ylmethyl)-carbamic acid tert-butyl ester To a solution of intermediate 12.ii (3.0 g) in THF (70 mL) was added LiAlH₄ (0.5 g). The mixture was stirred at the same temperature for 90 min. Water (1 mL), 2N NaOH (2.05 mL) and water (2.05 mL) were added. The mixture was stirred 30 min, diluted with EA (100 mL) and filtered. The solids were washed with EA (100 mL). The filtrate was concentrated to dryness and the residue was purified by CC (DCM-MeOH 93:7 containing 0.7% aq. NH₄OH) to afford the title compound as a yellowish foam (2.1 g).

MS (ESI, m/z): 435.4 [M+H⁺].

12.iv. (2RS)-3-((3S)-3-aminomethyl-pyrrolidin-1-yl)-2-(3-fluoro-6-methoxy-[1,5]naphthyridin-4-yl)-propan-1-ol Starting from intermediate 12.iii (2.0 g, 4.6 mmol); the title amine was obtained as a yellowish oil (1.2 g, 78% yield) using the procedure of Example 1, step 1.i. The crude material was carried on without purification.

MS (ESI, m/z): 335.1 [M+H⁺].

12.v. (2,3-dihydro-[1,4]dioxino[2,3-c]pyridin-7-ylmethyl)-[(3S)-1-((1RS)-8-methoxy-1,2-dihydro-3-oxa-5,9-diaza-cyclopenta[a]naphthalen-1-ylmethyl) -pyrrolidin-3-ylmethyl]-amine Starting from intermediate 12.iv (0.407 g, 1.21 mmol) and 2,3-dihydro -[1,4]dioxino[2,3-c]pyridine-7-carbaldehyde (0.201 g, 1.0 eq.), the title compound was obtained as a white foam (0.15 g) using the procedures of Example 1, steps 1.ii (reductive amination, 58% yield), 1.iii (N-Boc formation, 88% yield), 1.iv (cyclization using 1.2 eq. of t-BuOK at rt, 58% yield) and 1.v (Boc deprotection, 91% yield). The crude reaction mixtures were purified by CC using DCM-MeOH-aq. NH₄OH (9:1:0.1) as eluent.

MS (ESI, m/z): 464.1 [M+H⁺].

Example 13

[(E)-3-(2,5-difluoro-phenyl)-allyl]-[(3S)-1-((1RS)-8-methoxy-1,2-dihydro-3-oxa-5,9-diaza-cyclopenta[a] naphthalen-1-ylmethyl)-pyrrolidin-3-ylmethyl]-amine 13.i. (3S)-[(1RS)-1-(8-methoxy-1,2-dihydro-3-oxa-5,9-diaza-cyclopenta[a]naphthalen-1-ylmethyl)-pyrrolidin-3-ylmethyl]-carbamic acid tert-butyl ester To a solution of intermediate 12.iv (0.7 g, 2.1 mmol) in THF (30 mL) was added t-BuOK (0.52 g, 2.2 eq.). The mixture was stirred at rt for 4 h. Water (1 mL) and EA (50 mL) were added. The mixture was filtered through hydromatrix® and the filtrate was concentrated to dryness. The residue was taken up in DCM (15 mL) and di-tert-butyl dicarbonate (Boc₂O) (0.95 g) was added in one portion. The mixture was stirred at rt for 90 min. The solvent was evaporated and the residue was purified by CC (DCM-MeOH 19:1 containing 0.5% NH₄OH) to afford the title carbamate as a yellowish foam (0.4 g, 46% yield)

MS (ESI, m/z): 415.2 [M+H⁺]. .

13.ii. (3S)-[(1RS)-1-(8-methoxy-1,2-dihydro-3-oxa-5,9-diaza-cyclopenta[a]naphthalen-1-ylmethyl)-pyrrolidin-3-yl]-methylamine Starting from intermediate 13.i (0.4 g, 0.965 mmol); the title amine was obtained as a yellowish oil (0.245 g, 81% yield) using the procedure of Example 1, step 1.i. The crude material was purified by CC (DCM-MeOH 9:1 containing 1% aq. NH$_4$OH).

MS (ESI, m/z): 315.1 [M+H$^+$].

13.iii. [(E)-3-(2,5-difluoro-phenyl)-allyl]-[(3S)-1-((1RS)-8-methoxy-1,2-dihydro-3-oxa-5,9-diaza-cyclopenta[a]naphthalen-1-ylmethyl)-pyrrolidin-3-ylmethyl]-amine Starting from intermediate 13.ii (0.11 g, 0.35 mmol) and (E)-3-(2,5-difluoro-phenyl)-propenal (0.058 g, 1.0 eq.), the title compound was obtained as a yellowish oil (0.08 g, 49% yield) using the procedure of Example 1, step 1.ii. The crude material was purified by CC (DCM -MeOH 93:7 containing 0.7% aq. NH$_4$OH).

$^1$H NMR (CDCl$_3$) δ: 8.45 (s, 1H); 8.12 (d, J=9.3 Hz, 1H); 7.14 (m, 1H); 6.99 (m, 1H); 6.92 (overlapped d, J=9.3 Hz, 1H); 6.89 (m, 1H); 6.65 (d, J=16.2 Hz, 1H); 6.36 (td, J=6.0, 16.2 Hz, 1H); 4.78-4.86 (m, 2H); 4.12 (m, 1H); 4.06 (s, 3H); 3.45 (dd, J=1.5, 6.0 Hz, 1H); 3.30 (ddd, J=3.6, 8.4, 12.0 Hz, 1H); 2.52-2.84 (m, 5H); 2.26-2.48 (m, 2H);2.03 (m, 1H); 1.36-1.58 (m, 3H).

MS (ESI, m/z): 467.4 [M+H$^+$].

Example 14

6-({[(3S)-1-((1RS)-8-methoxy-1,2-dihydro-3-oxa-5,9-diaza-cyclopenta[a]naphthalen-1-ylmethyl)-pyrrolidin-3-ylmethyl]-amino}-methyl)-4H-pyrido[3,2-b][1,4]thiazin-3-one Starting from intermediate 13.ii (0.135 g, 0.429 mmol) and 3-oxo-3,4-dihydro-2H-pyrido[3,2-b][1,4]thiazine-6-carbaldehyde (0.083 g, 1.0 eq.), the title compound was obtained as a yellowish oil (0.115 g, 54% yield) using the procedure of Example 1, step 1.ii. The crude material was purified by CC (DCM-MeOH 93:7 containing 0.7% aq. NH$_4$OH).

$^1$H NMR (d6-DMSO) δ: 10.84 (s, 1H); 8.48 (s, 1H); 8.17 (d, J=9.3 Hz, 1H); 7.72 (dd, J=1.2, 8.1 Hz, 1H); 7.06 (d, J=8.1 Hz, 1H); 7.03 (d, J=9.3 Hz, 1H); 4.84 (td, J=3.6, 9.0 Hz, 1H); 4.66 (m, 1H); 4.12 (m, 1H); 4.00 (s, 3H); 3.67 (s, 2H); 3.17 (m, 1H); 2.55-2.78 (m, 3H); 2.05-2.50 (m, 6H); 1.86 (m, 1H); 1.40 (m, 1H).

MS (ESI, m/z): 493.1[M+H$^+$].

Example 15 rac-6-{[1-(2-methoxy-8,9-dihydro-furo[2,3-h]quinolin-9-ylmethyl)-piperidin-4-ylamino]-methyl}-4H-benzo[1,4]oxazin-3-one Starting from intermediate 3.ii (0.075 g, 0.287 mmol) and 3-oxo-3,4-dihydro-2H-benzo[1,4]oxazine-6-carbaldehyde (commercially available; 0.042 g, 1.0 eq.), the title compound was obtained as an off-white solid (0.074 g, 65% yield) using the procedure of Example 1, step 1.ii. The crude mixture was purified by CC (DCM-MeOH 93:7 containing 0.7% aq. NH$_4$OH).

$^1$H NMR (d6-DMSO) δ: 10.62 (s, 1H); 8.12 (d, J=9.0 Hz, 1H); 7.65 (d, J=8.7 Hz, 1H); 6.98 (d, J=8.7 Hz, 1H); 6.90 (s, 1H); 6.85-6.87 (m, 2H); 6.77 (d, J=9.0 Hz, 1H); 4.72 (t, J=9.0 Hz, 1H); 4.59 (overlapped dd, J=5.1, 9.0 Hz, 1H); 4.51 (s, 2H); 4.07 (m, 1H); 3.96 (s, 3H); 3.62 (s, 2H); 3.15 (dd, J=3.3, 12.6 Hz, 1H); 3.10 (overlapped m, 1H); 2.72 (m,1H); 2.32-2.46 (m, 2H); 2.11 (m, 1H); 1.99 (br s, 1H); 1.93 (m, 1H); 1.64-1.88 (m, 2H); 1.20-1.36 (m, 2H).

MS (ESI, m/z): 475.6 [M+H$^+$].

Examples 16A and 16B

6-{[1-((1R)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one and 6-{[1-((1S)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one The two title enantiomers (0.160 g each) were obtained by chiral HPLC separation of rac-6-{[1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one (Example 7, 0.480 g) on a semi-preparative ChiralPak IA column (20×250 mm). The elution was performed using a MeCN-EtOH-diethylamine (65-34.965-0.035) mixture. The respective retention times were 9.98 and 12.79 min.

Using an analytical Chiralpak IA column (4.6×250 mm), the respective retention times for the compounds of Examples 16A and 16B (eluent: MeCN-EtOH-diethylamine 65-34.965-0.035) were 11.6 and 21.3 min. The absolute stereochemistry of both enantiomers has not been assigned.

Example 17

6-{[(3S*,4R*)-3-fluoro-1-((1RS)-8-methoxy-1,2-dihydro-3-oxa-5,9-diaza -cyclopenta[a]naphthalen-1-ylmethyl)-piperidin-4-ylamino]-methyl}-4H-pyrido[3,2-b][1,4]thiazin-3-one

17.i. (2RS)-3-((3S*,4R*)-4-benzyloxycarbonylamino-3-fluoro-piperidin-1-yl)-2-(3-fluoro-6-methoxy-[1,5]naphthyridin-4-yl)-propionic acid ethyl ester Starting from intermediate 12.i (1.9 g, 6.87 mmol) and (3S*,4R*)-(3-fluoro-piperidin-4-yl) -carbamic acid benzyl ester (prepared as described in WO 2004/002490; 1.5 g, 1 eq.), the title compound was prepared as a colourless foam (3.1 g, 85% yield), using the procedure of Example 12, step 12.ii. The crude mixture was purified by CC using Hept-EA (1-3) containing 1% v/v of TEA.

MS (ESI, m/z): 529.3 [M+H$^+$].

17.ii. (2RS)-3-((3S*,4R*)-4-amino-3-fluoro-piperidin-1-yl)-2-(3-fluoro-6-methoxy-[1,5]naphthyridin-4-yl)-propionic acid ethyl ester To a solution of intermediate 17.i (3.1 g, 5.86 mmol) in EA (50 mL) was added 10% Pd/C (1.75 g). The reaction vessel was flushed twice with nitrogen and then twice with hydrogen. The reaction was stirred 3h under hydrogen atmosphere. The catalyst was removed by filtration and the filtrate was concentrated to dryness to afford the title amine as a colourless oil (2.31 g, 100% yield).

MS (ESI, m/z): 395.2 [M+H$^+$].

17. iii. (2RS)-3-((3S*,4R*)-4-tert-butoxycarbony-lamino-3-fluoro-piperidin-1-yl)-2-(3-fluoro-6-methoxy-[1,5]naphthyridin-4-yl)-propionic acid ethyl ester To a solution of intermediate 17.ii (2.31 g, 5.86 mmol) in DCM (50 mL) was added Boc₂O (2.6 g). The mixture was stirred at rt for 2 h. After concentration to dryness, the residue was chromatographed using Hept-EA (1:1) containing 1% v/v of TEA to afford the title compound as a white foam (2.30 g, 79% yield).

MS (ESI, m/z): 495.2 [M+H⁺].

17.iv. {[(3S*,4R*)-3-fluoro-1-[(2RS)-2-(3-fluoro-6-methoxy-[1,5]naphthyridin-4-yl)-3-hydroxy-propyl]-piperidin-4-yl}-carbamic acid tert-butyl ester To a solution of intermediate 17.iii (2.3 g, 4.65 mmol) in THF (55 mL) was added lithium aluminium hydride (0.36 g). The mixture was stirred at the same temperature for 45 min. Water (0.75 mL), 2N NaOH (1.5 mL) and water (0.75 mL) were added. The mixture was stirred 30 min, diluted with EA and filtered through Celite. The solids were washed with EA (100 mL). The filtrate was concentrated to dryness and the residue was purified by CC using Hept-EA (1:3) containing 1% v/v of TEA to afford the title compound as a yellowish foam (1.93 g, 93% yield).

MS (ESI, m/z): 453.4 [M+H⁺].

17.v. (2RS)-3-(3S*,4R*)-4-amino-3-fluoro-piperidin-1-yl)-2-(3-fluoro-6-methoxy-[1,5]naphthyridin-4-yl)-propan-1-ol Starting from intermediate 17.iv (1.93 g, 4.33 mmol), the title compound was obtained as a colourless foam (1.59 g, 100% yield) using the procedure of Example 1, step 1.i.

MS (ESI, m/z): 353.2 [M+H⁺].

17.vi. (3S*,4R*)-3-fluoro-1-((1RS)-8-methoxy-1,2-dihydro-3-oxa-5,9-diaza-cyclopenta[a]naphthalen-1-ylmethyl)-piperidin-4-ylamine To a solution of intermediate 17.iv (1.59 g, 4.51 mmol) in THF (50 mL) was added t-BuOK (1.1 g, 9.92 mmol). The reaction mixture was stirred at rt for 1 h. Water (10 mL) and 10% aq. NaHSO₄ (5 mL) was added. The volatiles were removed in vacuo and the residue was extracted five times with DCM-MeOH (9-1, 5×50 mL). The combined org. layers were washed with brine, dried over Na₂SO₄, filtered and concentrated to dryness. The residue was chromatographed (DCM-MeOH 93-7 containing 0.7% v/v aq. NH₄OH then DCM-MeOH 9:1 containing 1% aq. NH₄OH) to afford the title compound as a yellowish foam (0.7 g, 47% yield).

¹H NMR (CDCl₃) mixture of diastereomers δ: 8.45 (s, 1H); 8.12 (d, J=9.0 Hz, 1H); 6.92 (d, J=9.0 Hz, 1H); 4.85-4.75 (m, 2H); 4.68 (m, 0.5H); 4.51 (m, 0.5H); 4.15 (m, 1H); 4.03 (s, 3H); 3.26-3.40 (m, 1.5H); 2.70-3.10 (m, 2.5H); 2.28-2.64 (m, 2.5H); 2.19 (m, 0.5H); 1.68-1.88 (m, 2H); 1.446 (br. s, 2H).

MS (ESI, m/z): 333.1 [M+H⁺].

17.vii. 6-{[(3S*,4R*)-3-fluoro-1-((1RS)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one Starting from intermediate 17.vi (0.1 g, 0.318 mmol) and 3-oxo-3,4-dihydro-2H-pyrido[3,2-b][1,4]thiazine-6-carbaldehyde (0.062 g, 1.01 eq.), the title compound was obtained as an off-white foam (0.090 g, 55% yield) using the procedure of Example 1, step 1.ii. The crude mixture was purified by CC using as eluent DCM-MeOH (19-1) containing 0.5% v/v aq. NH₄OH.

¹H NMR (d6-DMSO) mixture of diastereomers δ: 10.85 (s, 1H); 8.48 (s, 1H); 8.18 (d, J=9.0 Hz, 1H); 7.72 (d, J=7.8 Hz, 1H); 7.10 (d, J=7.8 Hz, 1H); 7.03 (d, J=9.0 Hz, 1H); 4.78-4.88 (m, 1.5H); 4.64-4.72 (m, 1.5H); 4.18 (m, 1H); 3.99 (s, 3H); 3.77 (br. s, 2H); 3.52 (s, 2H); 3.26 (m, 1H); 3.04 (m, 1H); 2.02-2.80 (m, 6H); 1.57-1.77 (m, 2H).

MS (ESI, m/z): 511.2 [M+H⁺].

Example 18

6-{[(3S*,4R*)-3-fluoro-1-((1RS)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one Starting from intermediate 17.vi (0.1 g, 0.318 mmol) and 3-oxo-3,4-dihydro-2H-pyrido[3,2-b][1,4]oxazine-6-carbaldehyde (0.057 g, 1.01 eq.), the title compound was obtained as an off-white foam (0.070 g, 44% yield) using the procedure of Example 1, step 1.ii. The crude mixture was purified by CC using DCM-MeOH (19-1) containing 0.5% v/v aq. NH₄OH.

¹H NMR (d6-DMSO) mixture of diastereomers δ: 11.16 (br. s, 1H); 8.48 (s, 1H); 8.17 (d, J=9.0 Hz, 1H); 7.30 (d, J=8.1 Hz, 1H); 7.03 (d, J=9.0 Hz, 1H); 7.02 (d, J=8.1 Hz, 1H); 4.78-4.88 (m, 1.5H); 4.64-4.72 (m, 1.5H); 4.60 (s, 2H); 4.18 (m, 1H); 4.00 (s, 3H); 3.74 (br. s, 2H); 3.26 (m, 1H); 3.04 (m, 1H); 2.00-2.78 (m, 6H); 1.56-1.78 (m, 2H).

MS (ESI, m/z): 495.1 [M+H⁺].

Example 19

(2,3-dihydro-[1,4]dioxino[2,3-c]pyridin-7-ylmethyl)-[(3S*,4R*)-3-fluoro-1-((1RS)-8-methoxy-1,2-dihydro-3-oxa-5,9-diaza-cyclopenta[a]naphthalen-1-ylmethyl)-piperidin-4-yl]-amine Starting from intermediate 17.vi (0.1 g, 0.318 mmol) and 2,3-dihydro-[1,4]dioxino[2,3-c]pyridine-7-carbaldehyde (0.053 g, 1.01 eq.), the title compound was obtained as an off-white foam (0.030 g, 20% yield) using the procedure of Example 1, step 1.ii. The crude mixture was purified by CC using DCM-MeOH (19:1) containing 0.5% v/v aq. NH₄OH.

¹H NMR (d6-DMSO) δ: 8.48 (s, 1H); 8.17 (d, J=9.0 Hz, 1H); 8.00 (s, 1H); 7.03 (d, J=9.0 Hz, 1H); 6.95 (s, 1H); 4.77-4.85 (m, 1.5H); 4.62-4.71 (m, 1.5H); 4.31-4.36 (m, 2H); 4.29-4.25 (m 2H); 4.18 (m, 1H); 3.99 (s, 3H); 3.72 (br s, 2H); 3.26 (m, 1H); 3.02 (m, 1H); 1.96-2.78 (m, 6H); 1.55-1.73 (m, 2H).

MS (ESI, m/z): 482.2 [M+H⁺].

Example 20

(2,3-dihydro-[1,4]dioxino[2,3-c]pyridin-7-ylmethyl)-[(3-exo)-8-((1RS)-8-methoxy-1,2-dihydro-3-oxa-5,9-diaza-cyclopenta[a]naphthalen-1-ylmethyl)-8-aza-bicyclo[3.2.1]oct-3-yl]-amine

20.i. rac-(3-exo)-8-(8-methoxy-1,2-dihydro-3-oxa-5,9-diaza-cyclopenta[a]naphthalen-1-ylmethyl)-8-aza-bicyclo[3.2.1]oct-3-ylamine Starting from intermediate 12.i (1.97 g, 7.13 mmol) and ((3-exo)-8-aza-bicyclo[3.2.1]oct-3-yl)-carbamic acid tert-butyl ester (1.10 g, 4.86 mmol), the title compound was obtained as a colourless gum (0.142 g, 0.41 mmol) using the procedures of Example 12, step 12.ii and 12.iii (Michael addition, 36% yield and ester reduction, 68% yield), Example 1, step 1.i (Boc deprotection, 80% yield) and Example 12, step 12.iv (cyclization, 45% yield).

$^1$H NMR (CDCl$_3$) δ: 8.44 (s, 1H); 8.11 (d, J=9.3 Hz, 1H); 6.92 (d, J=9.3 Hz, 1H); 4.92 (m, 1H); 4.82 (m, 1H); 4.03 (s, 3H); 4.02 (overlapped m, 1H); 3.34-3.44 (m, 2H); 3.14 (m, 1H); 2.94 (m, 1H); 2.42 (m, 1H); 2.06-1.36 (m, 10H).

MS (ESI, m/z): 341.1 [M+H$^+$].

20.ii. (2,3-dihydro-[1,4]dioxino[2,3-c]pyridin-7-ylmethyl)-[(3-exo)-8-((1RS)-8-methoxy-1,2-dihydro-3-oxa-5,9-diaza-cyclopenta[a]naphthalen-1-ylmethyl)-8-aza-bicyclo[3.2.1]oct-3-yl]-amine Starting from intermediate 20.i (0.071 g, 0.21 mmol) and 2,3-dihydro-[1,4]dioxino[2,3-c]pyridine-7-carbaldehyde (0.035 g, 1.01 eq.), the title compound was obtained as an off-white foam (0.041 g, 40% yield) using the procedure of Example 1, step 1.ii. The crude mixture was purified by CC using DCM-MeOH (93:7) containing 0.7% v/v aq. NH$_4$OH.

MS (ESI, m/z): 490.3 [M+H$^+$].

Example 21

[(E)-3-(2,5-difluoro-phenyl)-allyl]-[(3-exo)-8-((1RS)-8-methoxy-1,2-dihydro-3-oxa-5,9-diaza-cyclopenta[a]naphthalen-1-ylmethyl)-8-aza -bicyclo [3.2.1]oct-3-yl]-amine Starting from intermediate 20.i (0.071 g, 0.21 mmol) and (E)-3-(2,5-difluoro-phenyl)-propenal (0.035 g, 1.01 eq.), the title compound was obtained as an off-white foam (0.053 g, 51% yield) using the procedure of Example 1, step 1.ii. The crude mixture was purified by CC using DCM-MeOH (93:7) containing 0.7% v/v aq. NH$_4$OH.

MS (ESI, m/z): 493.1 [M+H$^+$].

Example 22

6-{[(3-exo)-8-((1RS)-8-methoxy-1,2-dihydro-3-oxa-5,9-diaza -cyclopenta[a]naphthalen-1-ylmethyl)-8-aza-bicyclo[3.2.1]oct-3-ylamino]-methyl}-4H-pyrido[3,2-b][1,4]oxazin-3-one Starting from intermediate 20.i (0.0546 g, 0.161 mmol) and 3-oxo-3,4-dihydro-2H-pyrido[3,2-b][1,4]oxazine-6-carbaldehyde (0.031 g, 1.1 eq.), the title compound was obtained as a white solid (0.044 g, 55% yield) using the procedure of Example 1, step 1.ii. The crude mixture was purified by CC using DCM-MeOH (93:7) containing 0.7% v/v aq. NH$_4$OH.

$^1$H NMR (d6-DMSO) δ: 11.13 (br. s, 1H); 8.48 (s, 1H); 8.16 (d, J=9.0 Hz, 1H); 7.27 (d, J=8.1 Hz, 1H); 7.02 (d, J=9.0 Hz, 1H); 6.96 (d, J=8.1 Hz, 1H); 4.74-4.88 (m, 2H); 4.60 (s, 2H); 4.06 (m, 1H); 3.98 (s, 3H); 3.62 (s, 2H); 3.30-3.42 (m, 2H); 3.12 (m, 1H); 2.72 (m, 1H); 2.46 (overlapped m, 1H); 1.30-1.96 (m, 9H).

MS (ESI, m/z): 503.5 [M+H$^+$].

Example 23

6-{[(3-exo)-8-((1RS)-8-methoxy-1,2-dihydro-3-oxa-5,9-diaza -cyclopenta[a]naphthalen-1-ylmethyl)-8-aza-bicyclo[3.2.1]oct-3-ylamino]-methyl}-4H-pyrido[3,2-b][1,4]thiazin-3-one Starting from intermediate 20.i (0.0546 g, 0.161 mmol) and 3-oxo-3,4-dihydro-2H-pyrido[3,2-b][1,4]thiazine-6-carbaldehyde (0.034 g, 1.1 eq.), the title compound was obtained as a yellowish foam (0.049 g, 59% yield) using the procedure of Example 1, step 1.ii. The crude mixture was purified by CC using DCM-MeOH (93:7) containing 0.7% v/v aq. NH$_4$OH.

$^1$H NMR (d6-DMSO) δ: 10.81 (br. s, 1H); 8.48 (s, 1H); 8.17 (d, J=9.3 Hz, 1H); 7.70 (d, J=7.8 Hz, 1H); 7.05 (d, J=7.8 Hz, 1H); 7.03 (d, J=9.3 Hz, 1H); 4.74-4.87 (m, 2H); 4.04 (m, 1H); 3.99 (s, 3H); 3.65 (s, 2H); 3.51 (s, 2H); 3.30-3.42 (m, 2H); 3.12 (m, 1H); 2.72 (m, 1H); 2.51 (overlapped m, 1H); 1.32-1.94 (m, 9H).

MS (ESI, m/z): 519.4 [M+H$^+$].

Example 24

6-({[(2S)-4-((1RS)-8-methoxy-1,2-dihydro-3-oxa-5,9-diaz -cyclopenta[a]naphthalen-1-ylmethyl)-morpholin-2-ylmethyl]-amino}-methyl) -4H-pyrido[3,2-b][1,4]oxazin-3-one 24.i. C-[4-(8-methoxy-1,2-dihydro-3-oxa-5,9-diaza-cyclopenta[a]naphthalen-1-ylmethyl) -morpholin-2-yl]-methylamine Starting from intermediate 12.i (0.782 g, 2.83 mmol) and (2R) -morpholin-2-ylmethyl-carbamic acid tert-butyl ester (0.637 g, 1.04 eq.), the title compound was obtained as a yellowish foam (0.142 g, 0.41 mmol) using the procedures of Example 12, steps 12.ii and 12.iii (Michael addition, 81% yield and ester reduction, 89% yield), Example 1, step 1.i (Boc deprotection, 65% yield) and Example 12, step 12.iv (cyclization, 32% yield). The crude reaction mixtures were, if necessary, purified by CC using an appropriate eluent system. The compound was obtained as an equimolar mixture of epimers.

$^1$H NMR (CDCl$_3$) δ: 8.46 (s, 1H); 8.12 (d, J=9.0 Hz, 1H); 6.93 (d, J=9.0 Hz, 1H); 4.76-4.84 (m, 2H); 4.18 (m, 1H); 4.05 (s, 3H); 3.97 (m, 0.5H); 3.88 (m, 0.5H); 3.70 (app. td, J=2.1, 11.4 Hz, 1H); 3.52 (m, 1H); 3.31 (m, 1H); 2.98 (m, 1H); 2.50-2.82 (m, 4H); 2.36 (app. td, J=3.3, 11.1 Hz, 0.5H); 2.22 (app. td, J=3.0, 11.1 Hz, 0.5H); 2.10 (t, J=10.2 Hz, 0.5H); 1.96 (t, J=10.8 Hz, 0.5H); 1.47 (br. s, 2H).

MS (ESI, m/z): 331.1 [M+H$^+$].

24.ii. 6-({[(2S)-4-((1RS)-8-methoxy-1,2-dihydro-3-oxa-5,9-diaza-cyclopenta[a]naphthalen-1-ylmethyl)-morpholin-2-ylmethyl]-amino}-methyl)-4H-pyrido[3,2-b][1,4]oxazin-3-one Starting from intermediate 24.i (0.045 g, 0.137 mmol) and 3-oxo-3,4-dihydro-2H-pyrido[3,2-b][1,4]oxazine-6-carbaldehyde (0.027 g, 1.1 eq.), the title compound was obtained as a yellowish foam (0.020 g, 30% yield) using the procedure of Example 1, step 1.ii. The crude mixture was purified by CC using DCM-MeOH (93:7) containing 0.7% v/v aq. NH$_4$OH. The compound was obtained as an equimolar mixture of epimers.

MS (ESI, m/z): 493.1 [M+H$^+$].

Example 25

6-({[(2S)-4-((1RS)-8-methoxy-1,2-dihydro-3-oxa-5,9-diaz -cyclopenta[a]naphthalen-1-ylmethyl)-morpholin-2-ylmethyl]-amino}-methyl)-4H-pyrido[3,2-b][1,4]thiazin-3-one Starting from intermediate 24.i (0.045 g, 0.137 mmol) and 3-oxo-3,4-dihydro-2H-pyrido[3,2-b][1,4]thiazine-6-carbaldehyde (0.029 g, 1.1 eq.), the title compound was obtained as a yellowish foam (0.050 g, 72% yield) using the procedure of Example 1, step 1.ii. The crude mixture was purified by CC using DCM-MeOH (93:7) containing 0.7% v/v aq. NH$_4$OH. The compound was obtained as an equimolar mixture of epimers.

MS (ESI, m/z): 493.1 [M+H$^+$].

Example 26

(2,3-dihydro-[1,4]dioxino[2,3-c]pyridin-7-ylmethyl)-[(2S)-4-((1RS)-8-methoxy-1,2-dihydro-3-oxa-5,9-diaza-cyclopenta[a]naphthalen-1-ylmethyl)-morpholin-2-ylmethyl]-amine Starting from intermediate 24.i (0.045 g, 0.137 mmol) and 2,3-dihydro-[1,4]dioxino[2,3-c]pyridine-7-carbaldehyde (0.025 g, 1.1 eq.), the title compound was obtained as a white foam (0.037 g, 57% yield) using the procedure of Example 1, step 1.ii. The crude mixture was purified by CC using DCM-MeOH (93:7) containing 0.7% v/v aq. NH$_4$OH. The compound was obtained as an equimolar mixture of epimers.

MS (ESI, m/z): 480.4 [M+H$^+$].

Example 27

6-({[3S)-1-((1RS)-8-methoxy-1,2-dihydro-3-oxa-5,9-diaza-cyclopenta[a]naphthalen-1-ylmethyl)-piperidin-3-ylmethyl]-amino}-methyl)-4H-pyrido[3,2-b][1,4]oxazin-3-one 27.i. 2-(3-chloro-6-methoxy-[1,5]naphthyridin-4-yl)-acrylic acid ethyl ester Starting from 8-bromo-7-chloro-2-methoxy-[1,5]naphthyridine (41.75 g, 152.6 mmol) and diethyl malonate (70.2 mL, 3 eq.), the title compound was obtained as a white solid (31.35 g, 107.2 mmol) using the procedures reported in WO 2007/071936 for the analogous methyl ester.

$^1$H NMR (d6DMSO) δ: 8.90 (s, 1H); 8.33 (d, J=9.1 Hz, 1H); 7.30 (d, J=9.0 Hz, 1H); 6.79 (d, J=0.6 Hz, 1H); 6.12 (d, J=0.6 Hz, 1H); 4.15 (q, J=7.0 Hz, 2H); 3.89 (s, 3H); 1.10 (t, J=7.0 Hz, 3H).

MS (ESI, m/z): 293.2 [M+H$^+$].

27.ii. Benzyl-{1-[2-(3-chloro-6-methoxy-[1,5]naphthyridin-4-yl)-ethyl]-piperidin-3-ylmethyl}-carbamic acid tert-butyl ester Starting from intermediate 27.i (4 g, 13.67 mmol) and (3R)-piperidin-3-ylmethyl-carbamic acid tert-butyl ester (4.2 g, 1.43 eq.), the title compound was obtained as an off-white foam (3.25 g) using the procedures of Example 12, steps 12.ii (Michael addition, 91% yield) and 12.iii (ester reduction, 84% yield), Example 1, steps 1.i (Boc removal, 97% yield), 1.ii (reductive amination using benzaldehyde, 66% yield) and 1.iii. (N-Boc formation, 88% yield). The respective crude reaction mixtures were purified by CC, if necessary, using an appropriate eluent system.

MS (ESI, m/z): 555.2 [M+H$^+$].

27.iii. Benzyl-[1-(8-methoxy-1,2-dihydro-3-oxa-5,9-diaza-cyclopenta[a]naphthalen-1-ylmethyl)-piperidin-3-ylmethyl]-carbamic acid tert-butyl ester A mixture of intermediate 27.ii (2.40 g, 4.32 mmol), Cs$_2$CO$_3$ (2.12 g, 6.47 mmol), Pd(OAc)$_2$ (0.097 g, 0.43 mmol), rac-2-(di-tert-butylphosphino)-1,1'-binaphtyl (0.206 g, 0.52 mmol) was purged with nitrogen for 15 min, and toluene (8.5 mL) was introduced. The mixture was then heated to 70° C. for 23 h. The reaction mixture was partitioned between water (30 mL) and EA (70 mL). The two layers were separated and the aq. layer was extracted once with EA (40 mL). The combined org. layers were washed with brine (80 mL), dried over Na$_2$SO$_4$, filtered and concentrated to dryness. The residue was purified by CC (EA-Hept 1:1 containing 1% TEA) to give the title compound as a yellow foam (0.839 g, 38% yield).

MS (ESI, m/z): 519.5 [M+H$^+$].

27.iv. C-[(1RS)-1-(8-methoxy-1,2-dihydro-3-oxa-5,9-diaza-cyclopenta[a]naphthalen-1-ylmethyl)-piperidin-3-yl]-methylamine Starting from intermediate 27.iii (0.839 g, 1.61 mmol), the title compound was obtained as a colourless oil (0.417 g) using the procedures of Example 1, step 1.i (Boc deprotection, 93% yield) and Example 3, step 3.ii (hydrogenolysis, 84% yield). The respective crude reaction mixtures were purified by CC, if necessary, using an appropriate eluent system.

MS (ESI, m/z): 329.3 [M+H$^+$].

27.v. 6-({[(3S)-1-((1RS)-8-methoxy-1,2-dihydro-3-oxa-5,9-diaza-cyclopenta[a]naphthalen-1-ylmethyl)-piperidin-3-ylmethyl]-amino}-methyl)-4H-pyrido[3,2-b][1,4]oxazin-3-one Starting from intermediate 27.iv (0.061 g, 0.185 mmol) and 3-oxo-3,4-dihydro-2H-pyrido[3,2-b][1,4]oxazine-6-carbaldehyde (0.037 g, 1.1 eq.), the title compound was obtained as an off-white foam (0.051 g, 57% yield) using the procedure of Example 1, step 1.ii. The crude mixture was purified by CC using DCM-MeOH (93:7) containing 0.7% v/v aq. NH$_4$OH.

MS (ESI, m/z): 491.0 [M+H$^+$].

Example 28

6-({[(3S)-1-((1RS)-8-methoxy-1,2-dihydro-3-oxa-5,9-diaza-cyclopenta[a]naphthalen-1-ylmethyl)-piperidin-3-ylmethyl]-amino}-methyl)-4H-pyrido[3,2-b][1,4]thiazin-3-one Starting from intermediate 27.iv (0.1 g, 0.304 mmol) and 3-oxo-3,4-dihydro-2H-pyrido[3,2-b][1,4]thiazine-6-carbaldehyde (0.065 g, 1.1 eq.), the title compound was obtained as a beige foam (0.114 g, 57% yield) using the procedure of Example 1, step 1.ii. The crude mixture was purified by CC using DCM-MeOH (93:7) containing 0.7% v/v aq. NH$_4$OH.

MS (ESI, m/z): 507.2 [M+H$^+$].

Example 29

(2,3-dihydro-1,4]dioxino[2,3-c]pyridin-7-ylmethyl)-[(3S)-1-((1RS)-8-methoxy-1,2-dihydro-3-oxa-5,9-diaza-cyclopenta[a]naphthalen-1-ylmethyl)-piperidin-3-ylmethyl]-amine Starting from intermediate 27.iv (0.1 g, 0.304 mmol) and 2,3-dihydro-[1,4]dioxino[2,3-c]pyridine-7-carbaldehyde (0.055 g, 1.1 eq.), the title compound was obtained as an off-white foam (0.091 g, 63% yield) using the procedure of Example 1, step 1.ii. The crude mixture was purified by CC using DCM-MeOH (93:7) containing 0.7% v/v aq. NH$_4$OH.

MS (ESI, m/z): 478.0 [M+H$^+$].

Example 30

[(E)-3-(2,5-difluoro-phenyl)-allyl]-(3S)-1-((1RS)-8-methoxy-1,2-dihydro-3-oxa-5,9-diaza-cyclopenta[a]naphthalen-1-ylmethyl)-piperidin-3-ylmethyl]-amine Starting from intermediate 27.iv (0.07 g, 0.21 mmol) and (E)-3-(2,5-difluoro-phenyl)-propenal (0.039 g, 1.1 eq.), the title compound was obtained as an off-white foam (0.083 g, 81% yield) using the procedure of Example 1, step 1.ii. The crude mixture was purified by CC using DCM-MeOH (19:1) containing 0.5% v/v aq. $NH_4OH$.

$^1$H NMR (d6-DMSO) δ: 8.48 (s, 1H); 8.17 (d, J=9.0 Hz, 1H); 7.44 (m, 1H); 7.22 (m, 1H); 7.09 (m, 1H); 7.03 (d, J=9.0 Hz, 1H); 6.59 (dd, J=7.5, 16.5 Hz, 1H); 6.48 (m, 1H); 4.82 (app. td, J=3.6, 9.0 Hz, 1H); 4.66 (m, 1H); 4.19 (m, 1H); 3.99 (m, 3×0.5H); 3.99 (3×0.5H); 3.27-3.35 (m, 4H); 3.13-3.25 (m, 1.5H); 2.99 (m, 0.5H); 2.79 (m, 0.5H); 2.69 (m, 0.5H); 2.54 (overlapped m, 1H); 2.36-2.46 (m, 2H); 2.14 (m, 0.5H); 1.40-2.00 (m, 4.5H); 0.94 (m, 1H).

MS (ESI, m/z): 481.4 [M+H$^+$].

Example 31

6-({[(3S)-1-((1RS)-8-methoxy-1,2-dihydro-3-oxa-5,9-diaza-cyclopenta[a]naphthalen-1-ylmethyl)-piperidin-3-ylmethyl]-amino}-methyl)-4H-benzo[1,4]oxazin-3-one Starting from intermediate 27.iv (0.075 g, 0.21 mmol) and 3-oxo-3,4-dihydro-2H-benzo[1,4]oxazine-6-carbaldehyde (0.041 g, 1.1 eq.), the title compound was obtained as an off-white foam (0.084 g, 80% yield) using the procedure of Example 1, step 1.ii. The crude mixture was purified by CC using DCM-MeOH (19:1) containing 0.5% v/v aq. $NH_4OH$.

$^1$H NMR (d6-DMSO) δ: 10.63 (s, 1H); 8.48 (s, 1H); 8.17 (d, J=9.0 Hz, 1H); 7.04 (d, J=9.0 Hz, 1H); 6.82-6.89 (m, 3H); 4.81 (app. t, J=9.0 Hz, 1H); 4.65 (dd, J=5.7, 9.0 Hz, 1H); 4.51 (s, 2×0.5H); 4.50 (s, 2×0.5H); 4.19 (m, 1H); 3.99 (s, 3H); 3.57 (s, 2×0.5H); 3.24-3.14 (m, 2×0.5H); 3.11 (m, 0.5H); 2.99 (m, 0.5H); 2.79 (m, 0.5H); 2.64 (m, 0.5H); 2.53 (overlapped m, 1H); 2.30-2.40 (m, 2.5H); 2.13 (m, 0.5H); 1.84-2.02 (m, 2H); 1.36-1.74 (m, 5H); 0.92 (m,1H).

MS (ESI, m/z): 490.3 [M+H$^+$].

Example 32

6-{[(1α,5α,6α)-3-((1RS)-8-methoxy-1,2-dihydro-3-oxa-5,9-diaza-cyclopenta[a]naphthalen-1-ylmethyl)-3-aza-bicyclo[3.1.0]hex-6-ylamino]-methyl}-4H-pyrido[3,2-b][1,4]oxazin-3-one

32.i. (1α,5α,6α)-3-((1RS)-8-methoxy-1,2-dihydro-3-oxa-5,9-diaza-cyclopenta[a]naphthalen-1-ylmethyl)-3-aza-bicyclo[3.1.0]hex-6-ylamine Starting from intermediate 27.i (3 g, 10.25 mmol) and (1a,5a,6a)-3-aza-bicyclo[3.1.0]hex-6-yl)-carbamic acid tert-butyl ester (2.43 g, 1.2 eq.), the title compound (0.48 g) was prepared as a waxy solid using sequentially the procedures of Example 12, steps 12.ii (Michael addition, 94% yield) and 12.iii (ester reduction, 70% yield), Example 1, steps 1.i (Boc removal, 90% yield), 1.ii. (reductive amination using benzaldehyde, 99% yield) and 1.iii (N-Boc formation, 87% yield), Example 25, step 25.iii (cyclization, 54% yield), Example 1, step 1.i (Boc deprotection, 100% yield) and Example 3, step 3.ii (hydrogenolysis, 62% yield). The respective crude reaction mixtures were purified by CC, if necessary, using an appropriate eluent system.

MS (ESI, m/z): 313.4[M+H$^+$].

32.ii. 6-{[(1α,5α,6α)-3-((1RS)-8-methoxy-1,2-dihydro-3-oxa-5,9-diaza-cyclopenta[a]naphthalen-1-ylmethyl)-3-aza-bicyclo[3.1.0]hex-6-ylamino]-methyl}-4H-pyrido[3,2-b][1,4]oxazin-3-one Starting from intermediate 32.i (0.090 g, 0.288 mmol) and 3-oxo-3,4-dihydro-2H-pyrido[3,2-b][1,4]oxazine-6-carbaldehyde (0.051 g, 1.01 eq.), the title compound was obtained as a white solid (0.017 g, 13% yield) using the procedure of Example 1, step 1.ii. The crude mixture was purified by CC using DCM-MeOH (93:7) containing 0.7% v/v aq. $NH_4OH$.

MS (ESI, m/z): 475.0 [M+H$^+$].

Example 33

(2,3-dihydro-[1,4]dioxino[2,3-c]pyridin-7-ylmethyl)-[(1α,5α,6α)-3-((1RS)-8-methoxy-1,2-dihydro-3-oxa-5,9-diaza-cyclopenta[a]naphthalen-1-ylmethyl)-3-aza-bicyclo[3.1.0]hex-6-yl]amine Starting from intermediate 32.i (0.090 g, 0.288 mmol) and 2,3-dihydro-[1,4]dioxino[2,3-c]pyridine-7-carbaldehyde (0.047 g, 1.1 eq.), the title compound was obtained as an off-white foam (0.036 g, 27% yield) using the procedure of Example 1, step 1.ii. The crude mixture was purified by CC using DCM-MeOH (93:7) containing 0.7% v/v aq. $NH_4OH$.

$^1$H NMR (d6-DMSO) δ: 8.46 (s, 1H); 8.17 (d, J=9.1 Hz, 1H); 8.00 (s, 1H); 7.03 (d, J=9.1 Hz 1H); 6.87 (s, 1H); 4.78 (t, J=8.8 Hz, 1H); 4.56 (td, J=5.9, 9.1 Hz, 1H); 4.32-4.36 (m, 2H); 4.26-4.30 (m, 2H); 4.03 (m, 1H); 4.00 (s, 3H); 3.62 (s, 2H); 3.15 (dd, J=3.5, 12.0 Hz, 1H); 3.08 (d, J=8.5 Hz, 1H); 2.81 (d, J=8.5 Hz, 1H); 2.67 (dd, J=10.0, 11.7 Hz, 1H); 2.34-2.41 (m, 2H); 2.25 (m, 1H); 1.28-1.39 (m, 2H); 1.23 (br. s, 1H).

MS (ESI, m/z): 462.0 [M+H$^+$].

Example 34

6-{[(1α,5α,6α)-3-((1RS)-8-methoxy-1,2-dihydro-3-oxa-5,9-diaza-cyclopenta[a]naphthalen-1-ylmethyl)-3-aza-bicyclo[3.1.0]hex-6-ylamino]-methyl}-4H-pyrido[3,2-b][1,4]thiazin-3-one Starting from intermediate 32.i (0.090 g, 0.288 mmol) and 3-oxo-3,4-dihydro-2H-pyrido[3,2-b][1,4]thiazine-6-carbaldehyde (0.056 g, 1.1 eq.), the title compound was obtained as an off-white foam (0.011 g, 8% yield) using the procedure of Example 1, step 1.ii. The crude mixture was purified by CC using DCM-MeOH (93:7) containing 0.7% v/v aq. $NH_4OH$.

MS (ESI, m/z): 491.2 [M+H$^+$].

Example 35 rac-6-{[1-(8-fluoro-1,2-dihydro-furo[2,3-c]quinolin-1-ylmethyl)-piperidin-4-ylamino]-methyl}-4H-pyrido[3,2-b][1,4]oxazin-3-one

35.i. 2-(6-fluoro-quinolin-4-yl)-malonic acid diethyl ester

To a suspension of NaH (60% in oil dispersion, 2.2 g, 54 mmol) in 1,4-dioxane (26 mL) was added diethyl malonate (9 mL, 59 mmol). The reaction mixture was stirred at rt for 5 min and heated at 80° C. for 1 h. After cooling to rt, CuBr (1.0 g) and 4-bromo-3-chloro-6-fluoro-quinoline (5 g, 19.4 mmol) in dioxane (8 mL) were successively added. The mixture was stirred at 100° C. overnight. After cooling, 10% aq. NaHSO$_4$ (100 mL) was added. The mixture was stirred 30 min. The two layers were decanted and the aq. layer was extracted three times with EA (3×150 mL). The combined org. layers were washed with brine, dried over Na$_2$SO$_4$, filtered and concentrated to dryness. The residue was triturated in DCM to yield the title compound as a yellow solid (6.71 g, 100% yield).

MS (ESI, m/z): 340.1 [M+H$^+$].

35.ii. (3-chloro-6-fluoro-quinolin-4-yl)-acetic acid ethyl ester

To a solution of intermediate 35.i (6.42 g, 18.9 mmol) in DMSO (50 mL), was added 6N HCl (6.61 mL). The mixture was stirred at 100° C. during 2 h. The mixture was cooled to 0° C. and aq. NaHCO$_3$ (44 mL) was added. The resulting mixture was stirred at this temperature for 10 min. The solids were filtered off, washed with water, air-dried and dried under HV to afford the title ester as a beige solid (3.87 g, 76% yield).

MS (ESI, m/z): 268.1 [M+H$^+$].

35.iii. 2-(3-chloro-6-fluoro-quinolin-4-yl)-acrylic acid ethyl ester

To a solution of intermediate 35.ii (3.74 g, 13.95 mmol) in cyclohexane (115 mL) were added benzyltriethylammonium chloride (98%, 6.32 g, 27.21 mmol, 1.95 eq.), K$_2$CO$_3$ (3.47 g, 25.12 mmol, 1.8 eq.) and paraformaldehyde (3.73 g, 120 mmol, 8.6 eq.). The mixture was heated to 80° C. overnight. After cooling, the reaction mixture was diluted with water (100 mL). After separation, the aq. layer was extracted with EA (2×20 mL). The combined org. layers were washed with brine (40 mL), dried over Na$_2$SO$_4$, filtered and concentrated to dryness. The residue was purified by CC (EA-Hept 1:4) to afford the title alkene as a colourless oil (3.15 g).

MS (ESI, m/z): 280.4 [M+H$^+$].

35.iv. 1-(8-fluoro-1,2-dihydro-furo[2,3-c]quinolin-1-ylmethyl)-piperidin-4-ylamine Starting from intermediate 35.iii (3.24 g, 11.6 mmol) and piperidin-4-yl-carbamic acid tert-butyl ester (3.48 g, 1.5 eq.), the title compound was obtained as a yellowish waxy solid (0.087 g) using sequentially the procedures of Example 12, steps 12.ii (Michael addition, 65% yield) and 12.iii (ester reduction, 73% yield), Example 1, steps 1.i (Boc removal, 91% yield), 1.ii (reductive amination using benzaldehyde, 99% yield) and 1.iii (N-Boc formation, 83% yield), Example 25, step 25.iii (cyclization, 25% yield), Example 1, step 1.i (Boc deprotection, 52% yield) and Example 3, step 3.ii (hydrogenolysis, 90% yield). The respective crude reaction mixtures were purified by CC, if necessary, using an appropriate eluent system.

MS (ESI, m/z): 302.1 [M+H$^+$].

35.v. rac-6-{[1-(8-fluoro-1,2-dihydro-furo[2,3-c]quinolin-1-ylmethyl)-piperidin-4-ylamino]-methyl}-4H-pyrido[3,2-b][1,4]oxazin-3-one Starting from intermediate 35.iv (0.0820 g, 0.272 mmol) and 3-oxo-3,4-dihydro-2H-pyrido[3,2-b][1,4]oxazine-6-carbaldehyde (0.0496 g, 1.01 eq.), the title compound was obtained as a beige solid (0.061 g, 48% yield) using the procedure of Example 1, step 1.ii. The crude mixture was purified by CC using DCM-MeOH (93:7) containing 0.7% v/v aq. NH$_4$OH.

MS (ESI, m/z): 464.3 [M+H$^+$].

Example 36

6-{(3R*,4S*)-[3-hydroxymethyl-1-((1RS)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one

36.i. (1RS)-3-((3R*,4S*)-4-amino-3-hydroxymethyl-piperidin-1-yl)-2-(3-fluoro-6-methoxy-[1,5]naphthyridin-4-yl)-propan-1-ol Starting from intermediate 12.i (1.66 g, 6.01 mmol) and (3R*,4S*)-4-benzyloxycarbonylamino-piperidine-3-carboxylic acid ethyl ester (1.93 g, 1.1 eq.), the title compound was obtained as an off-white foam (1.04 g) using sequentially the procedures of Example 12, steps 12.ii. and 12.iii (Michael addition, 91% yield and ester reduction, 68% yield) and Example 3, step 3.ii (hydrogenolysis, 79% yield). The crude reaction mixtures were, if necessary, purified by CC using an appropriate eluent system. The compound was obtained as a mixture of four diastereomers.

MS (ESI, m/z): 365.2 [M+H$^+$].

36.ii. [(3R*,4S*)-4-amino-1-((1RS)-8-methoxy-1,2-dihydro-3-oxa-5,9-diaza-cyclopenta[a]naphthalen-1-ylmethyl)-piperidin-3-yl]-methanol To a solution of intermediate 36.i (0.735 g, 2.02 mmol) in acetone (8 mL) was added 2-methoxypropene (1.708 mL, 18.14 mmol). The solution was stirred at rt for 100 min. More 2-methoxypropene (1 mL) was added and the reaction proceeded further for 40 min. The solvents were removed in vacuo to give an off-white foam. The latter was taken up in THF (20 mL) and treated with t-BuOK (0.497 g, 4.21 mmol). The reaction mixture was stirred at rt for 2 h. EA (20mL) and sat. aq. NaHCO$_3$ (15 mL) were added. The phases were separated. The pH of the aq. layer was adjusted to 12 by addition of 2M NaOH and the aq. layer was extracted 4 times with DCM-MeOH (9:1, 4×15 mL). The combined org. layers were dried over Na$_2$SO$_4$, filtered and evaporated under reduced pressure. The residue was purified by CC (DCM-MeOH 9:1 containing 1% aq. NH$_4$OH) to afford the title compound as a white foam (0.396 g, 55% yield).

$^1$H NMR (CDCl$_3$) δ: 8.45 (s, 1H); 8.11 (d, J=9.1 Hz, 1H); 6.91 (d, J=9.1 Hz, 1H); 4.69-4.85 (m, 2H); 4.16 (m, 1H); 4.04 (s, 3H); 4.01 (overlapped m, 1H); 3.88 (td, J=3.0, 11.1 Hz, 1H); 3.49 (br. s, 1H); 3.15-3.27 (m, 1H); 3.00 (m, 1H); 1.70-2.70 (m, 10H).

MS (ESI, m/z): 345.3 [M+H$^+$].

36.iii. 6-{(3R*,4S*)-[3-hydroxymethyl-1-((1RS)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one Starting from intermediate 36.iii (0.095 g, 0.278 mmol) and 3-oxo-3,4-dihydro-2H-pyrido[3,2-b][1,4]thiazine-6-carbaldehyde (0.060 g, 1.1 eq.), the title compound was obtained as a beige foam (0.022 g, 15% yield) using the procedure of Example 1, step 1.ii. The crude mixture was purified by CC using DCM-MeOH (93:7) containing 0.7% v/v aq. NH$_4$OH.

¹H NMR (d6DMSO) δ: 10.85 (s, 1H); 8.48 (s, 1H); 8.17 (d, J=9.0 Hz, 1H); 7.72 (d, J=7.8 Hz, 1H); 7.08 (d, J=7.8 Hz, 1H); 7.03 (d, J=9.0 Hz, 1H); 4.82 (td, J=4.9, 9.0 Hz, 1H); 4.68 (ddd, J=5.7, 9.0, 12.9 Hz, 1H); 4.18 (m, 1H); 4.00 (s, 3H); 3.70-3.75 (m, 2H); 3.63 (m, 1H); 3.57 (m, 1H); 3.53 (s, 2H); 3.18 (td, J=3.6, 12.3 Hz, 1H); 2.92 (m, 1H); 2.70 (m, 1H); 2.59 (m, 1H); 2.50 (overlapped m, 1H); 2.22-2.42 (m, 2H); 2.11 (m, 1H); 1.89 (m, 1H); 1.50-1.69 (m, 3H).
MS (ESI, m/z): 523.2 [M+H⁺].

Example 37

6-{(3R*,4S*)-[3-hydroxymethyl-1-((1RS)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one Starting from intermediate 36.iii (0.103 g, 0.3 mmol) and 3-oxo-3,4-dihydro-2H-pyrido[3,2-b][1,4]oxazine-6-carbaldehyde (0.060 g, 1.1 eq.), the title compound was obtained as a beige foam (0.024 g, 16% yield) using the procedure of Example 1, step 1.ii. The crude mixture was purified by CC using DCM-MeOH (93:7) containing 0.7% v/v aq. NH₄OH.
¹H NMR (d6DMSO+D₂O) δ: 8.46 (s, 1H); 8.16 (d, J=9.0 Hz, 1H); 7.29 (dd, J=0.9, 7.8 Hz, 1H); 7.02 (d, J=9.0 Hz, 1H); 7.00 (d, J=7.8 Hz, 1H); 4.84 (m, 1H); 4.68 (m, 1H); 4.60 (s, 2H); 4.16 (m, 1H); 3.98 (s, 3H); 3.60-3.67 (m, 3H); 3.55 (m, 1H); 3.16 (m, 1H); 2.92 (m, 1H); 2.44-2.68 (m, 3H); 2.32 (m, 1H); 2.09 (m, 1H); 1.88 (m, 1H); 1.48-1.60 (m, 2H).
MS (ESI, m/z): 507.2 [M+H⁺].

Example 38

(3R*,4S*)-[4-[(6,7-dihydro-[1,4]dioxino[2,3-c]pyridazin-3-ylmethyl)-amino]-1-((1RS)-8-methoxy-1,2-dihydro-3-oxa-5,9-diaza-cyclopenta[a]naphthalen-1-ylmethyl)-piperidin-3-yl]-methanol Starting from intermediate 36.iii (0.106 g, 0.31 mmol) and 6,7-dihydro-[1,4]dioxino[2,3-c]pyridazine-3-carbaldehyde (0.056 g, 1.1 eq.), the title compound was obtained as a white foam (0.023 g, 15% yield) using the procedure of Example 1, step 1.ii. The crude mixture was purified by CC using DCM-MeOH (93:7) containing 0.7% v/v aq. NH₄OH.
MS (ESI, m/z): 495.1 [M+H⁺].

Example 39

(6,7-dihydro-[1,4]dioxino[2,3-c]pyridazin-3-ylmethyl)-[(3S)-1-((1RS)-8-methoxy-1,2-dihydro-3-oxa-5,9-diaza-cyclopenta[a]naphthalen-1-ylmethyl)-piperidin-3-ylmethyl]-amine Starting from intermediate 27.iv (0.077 g, 0.23 mmol) and 6,7-dihydro-[1,4]dioxino[2,3-c]pyridazine-3-carbaldehyde (0.043 g, 1.1 eq.), the title compound (0.034 g, 30% yield) was obtained as an off-white foam using the procedure of Example 1, step 1.ii. The crude mixture was purified by CC using DCM-MeOH (19:1) containing 0.5% v/v aq. NH₄OH.
MS (ESI, m/z): 479.3 [M+H⁺].

Example 40

[4-[(2,3-dihydro-[1,4]dioxino[2,3-c]pyridin-7-ylmethyl)-amino]-1-((S)-8-methoxy-1,2-dihydro-3-oxa-5,9-diaza-cyclopenta[a]naphthalen-1-ylmethyl)-piperidin-3-yl]-methanol Starting from intermediate 36.iii (0.108 g, 0.31 mmol) and 2,3-dihydro-[1,4]dioxino[2,3-c]pyridine-7-carbaldehyde (0.056 g, 1.1 eq.), the title compound was obtained as a white foam (0.023 g, 15% yield) using the procedure of Example 1, step 1.ii. The crude mixture was purified by CC using DCM-MeOH (93:7) containing 0.7% v/v aq. NH₄OH.
MS (ESI, m/z): 494.1 [M+H⁺].

Pharmacological Properties of the Invention Compounds:
In vitro Assays
Experimental Methods:
These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards: Villanova, Pa., USA, 1997". Minimal inhibitory concentrations (MICs; mg/l) were determined in cation-adjusted Mueller-Hinton Broth by a microdilution method following NCCLS guidelines (National Committee for Clinical Laboratory Standards. Methods for Dilution Antimicrobial Susceptibility). The pH of the test medium was 7.2-7.3.

Results:
All Example compounds were tested against several Gram positive and Gram negative bacteria such as *S. aureus, E. faecalis, S. pneumoniae, M. catarrhalis* or *E.coli*.
Antibacterial test results are given in the table hereafter (MIC in mg/l).

| Compound of Example | M.catarrhalis A894 | Compound of Example | M. catarrhalis A894 | Compound of Example | M. catarrhalis A894 |
|---|---|---|---|---|---|
| 1 | ≦0.031 | 2 | ≦0.031 | 3 | ≦0.031 |
| 4 | ≦0.031 | 5 | ≦0.031 | 6 | ≦0.031 |
| 7 | ≦0.031 | 8 | ≦0.031 | 9 | ≦0.031 |
| 10 | ≦0.031 | 11 | 0.125 | 12 | ≦0.031 |
| 13 | ≦0.031 | 14 | ≦0.031 | 15 | ≦0.031 |
| 16A | ≦0.031 | 16B | ≦0.031 | 17 | ≦0.031 |
| 18 | ≦0.031 | 19 | ≦0.031 | 20 | ≦0.031 |
| 21 | ≦0.031 | 22 | ≦0.031 | 23 | ≦0.031 |
| 24 | ≦0.031 | 25 | ≦0.031 | 26 | ≦0.031 |
| 27 | ≦0.031 | 28 | ≦0.031 | 29 | ≦0.031 |
| 30 | ≦0.031 | 31 | ≦0.031 | 32 | ≦0.031 |
| 33 | ≦0.031 | 34 | ≦0.031 | 35 | ≦0.031 |
| 36 | ≦0.031 | 37 | ≦0.031 | 38 | 0.063 |
| 39 | ≦0.031 | 40 | ≦0.031 | | |

The invention claimed is:

1. A compound of formula (I)

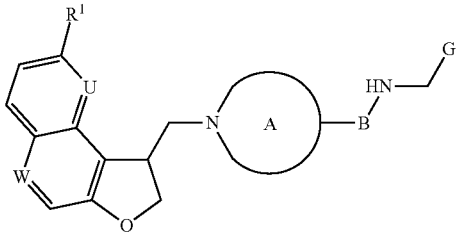

wherein
U represents CH or N;
W represents CH or N;
R¹ represents alkoxy, halogen, or CN;
ring A represents a pyrrolidin-1,3-diyl-, a piperidin-1,3-diyl, or a morpholin-2,4-diyl group and B represents CH₂; or
ring A is A¹, A², or A³ drawn below:

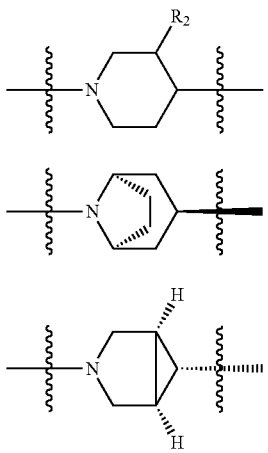

wherein R² represents H, F, or hydroxymethyl, and B is absent;
G represents

wherein Z represents CH or N; and
Q represents O or S;
or a salt thereof.

2. The compound according to claim 1, wherein one of U and W represents CH or N and the other represents N; or a salt thereof.

3. The compound according to claim 1,
wherein
U represents N;
W represents CH or N;
R¹ represents (C₁-C₄)alkoxy or CN;
ring A represents a pyrrolidin-1,3-diyl, a piperidin-1,3-diyl or a morpholin-2,4-diyl group and B represents CH₂; or
ring A represents a piperidin-1,4-diyl group and B is absent;
G represents

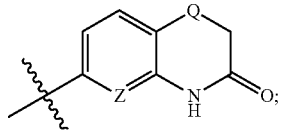

wherein Z represents CH or N; and
or a salt thereof.

4. The compound according to claim 1, wherein R¹ represents alkoxy; or a salt thereof.

5. The compound according to claim 1, wherein
ring A represents a pyrrolidin-1,3-diyl group and B represents CH₂; or ring A represents a piperidin-1,4-diyl group and B is absent; or a salt thereof.

6. The compound according to claim 1, wherein ring A is A¹, A², or A³; or a salt thereof.

7. The compound according to claim 1, which is
6-{[1-(2-methoxy-8,9-dihydro-furo[2,3-h]quinolin-9-yl-methyl)-piperidin-4-ylamino]-methyl}-4H-pyrido[3,2-b][1,4]thiazin-3-one;
6-{[1-(2-methoxy-8,9-dihydro-furo[2,3-h]quinolin-9-yl-methyl)-piperidin-4-ylamino]-methyl}-4H-pyrido[3,2-b][1,4]oxazin-3-one;
6-{[1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one;
6-{[1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one;
6-({[(3S)-1-(8-methoxy-1,2-dihydro-3-oxa-5,9-diaza-cyclopenta[a]naphthalen-1-ylmethyl)-pyrrolidin-3-ylmethyl]-amino}-methyl)-4H-pyrido[3,2-b][1,4]thiazin-3-one;
6-{[1-(2-methoxy-8,9-dihydro-furo[2,3-b]quinolin-9-yl-methyl)-piperidin-4-ylamino]-methyl}-4H-benzo[1,4]oxazin-3-one;
6-{[1-((1R)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one;
6-{[1-((1S)-8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one;
6-{[(3S*,4R*)-3-fluoro-1-(8-methoxy-1,2-dihydro-3-oxa-5,9-diaza-cyclopenta[1]naphthalen-1-ylmethyl)-piperidin-4-ylamino]-methyl}-4H-pyrido[3,2-b][1,4]thiazin-3-one;
6-{[(3S*,4R*)-3-fluoro-1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one;
6-{[(3-exo)-8-(8-methoxy-1,2-dihydro-3-oxa-5,9-diaza-cyclopenta[a]naphthalen-1-ylmethyl)-8-aza-bicyclo[3.2.1]oct-3-ylamino]-methyl}-4H-pyrido[3,2-b][1,4]oxazin-3-one;
6-{[(3-exo)-8-(8-methoxy-1,2-dihydro-3-oxa-5,9-diaza-cyclopenta[a]naphthalen-1-ylmethyl)-8-aza-bicyclo[3.2.1]oct-3-ylamino]-methyl}-4H-pyrido[3,2-b][1,4]thiazin-3-one;

6-({[(2S)-4-(8-methoxy-1,2-dihydro-3-oxa-5,9-diaza-cyclopenta[a]naphthalen-1-ylmethyl)-morpholin-2-ylmethyl]-amino}-methyl)-4H-pyrido[3,2-b][1,4]oxazin-3-one;

6-({[(2S)-4-(8-methoxy-1,2-dihydro-3-oxa-5,9-diaza-cyclopenta[a]naphthalen-1-ylmethyl)-morpholin-2-ylmethyl]-amino}-methyl)-4H-pyrido[3,2-b][1,4]thiazin-3-one;

6-({[(3S)-1-(8-methoxy-1,2-dihydro-3-oxa-5,9-diaza-cyclopenta[a]naphthalen-1-ylmethyl)-piperidin-3-ylmethyl]-amino}-methyl)-4H-pyrido[3,2-b][1,4]oxazin-3-one;

6-({[(3S)-1-(8-methoxy-1,2-dihydro-3-oxa-5,9-diaza-cyclopenta[a]naphthalen-1-ylmethyl)-piperidin-3-ylmethyl]-amino}-methyl)-4H-pyrido[3,2-b][1,4]thiazin-3-one;

6-({[(3S)-1-(8-methoxy-1,2-dihydro-3-oxa-5,9-diaza-cyclopenta[a]naphthalen-1-ylmethyl)-piperidin-3-ylmethyl]-amino}-methyl)-4H-benzo[1,4]oxazin-3-one;

6-{[(1□,5□,6□)-3-(8-methoxy-1,2-dihydro-3-oxa-5,9-diaza-cyclopenta[a]naphthalen-1-ylmethyl)-3-aza-bicyclo[3.1.0]hex-6-ylamino]-methyl}-4H-pyrido[3,2-b][1,4]oxazin-3one;

6-{[(1□,5□,6□)-3-(8-methoxy-1,2-dihydro-3-oxa-5,9-diaza-cyclopenta[a]naphthalen-1-methyl)-3-aza-bicyclo[3.1.0]hex-6-ylamino]-methyl}-4H-pyrido[3,2-b][1,4]thiazin-3-one;

6-{[1-(8-fluoro-1,2-dihydro-furo[2,3-c]quinolin-1-ylmethyl)-piperidin-4-ylamino]-methyl}-4H-pyrido[3,2-b][1,4]oxazin-3-one;

6-{(3R*,4S *)-[3-hydroxymethyl-1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]thiazin-3-one;

6-{(3R*,4S *)-[3-hydroxymethyl-1-(8-methoxy-1,2-dihydro-3-oxa-5,9-diaza-cyclopenta[a]naphthalen-1-ylmethyl)-piperidin-4-ylamino]-methyl}-4H-pyrido[3,2-b][1,4]oxazin-3-one;

or a salt thereof.

8. A pharmaceutical composition comprising as active principle, a compound according to claim 1, or a pharmaceutically acceptable salt thereof, and at least one therapeutically inert excipient.

9. A method of treating a bacterial infection comprising administering, to a subject in need thereof, a pharmaceutical composition according to claim 8.

10. A method for treating a bacterial infection comprising administering, to a subject in need thereof, a compound according to claim 1 or a pharmaceutically acceptable salt thereof.

11. The compound according to claim 1, wherein Z represents CH; or a salt thereof.

12. The compound according to claim 1, wherein Z represents N; or a salt thereof.

13. The compound according to claim 1, wherein Q represents O; or a salt thereof.

14. The compound according to claim 1, wherein Q represents S; or a salt thereof.

* * * * *